US007918790B2

(12) United States Patent
Ikeda et al.

(10) Patent No.: US 7,918,790 B2
(45) Date of Patent: Apr. 5, 2011

(54) ELECTRIC BENDING ENDOSCOPE

(75) Inventors: Yuichi Ikeda, Tama (JP); Keiichi Arai, Hachioji (JP); Takemitsu Honda, Hino (JP); Seiichiro Kimoto, Hachioji (JP); Takayasu Miyagi, Hachioji (JP); Toshinari Maeda, Hachioji (JP); Toshimasa Kawai, Yokohama (JP)

(73) Assignee: Olympus Corporation, Tokyo (JP)

( * ) Notice: Subject to any disclaimer, the term of this patent is extended or adjusted under 35 U.S.C. 154(b) by 1097 days.

(21) Appl. No.: 11/649,530

(22) Filed: Jan. 4, 2007

(65) Prior Publication Data

US 2007/0112255 A1    May 17, 2007

Related U.S. Application Data

(63) Continuation of application No. 10/403,128, filed on Mar. 31, 2003, now abandoned.

(30) Foreign Application Priority Data

Feb. 7, 2002 (JP) .................................. 2002-31429

(51) Int. Cl.
*A61B 1/00* (2006.01)

(52) U.S. Cl. ....................................... 600/152; 600/146

(58) Field of Classification Search .......... 600/145–146, 600/148–150, 152
See application file for complete search history.

(56) References Cited

U.S. PATENT DOCUMENTS

| 4,525,763 | A | 6/1985 | Hardy et al. |
| 4,982,725 | A | 1/1991 | Hibino et al. |
| 5,060,632 | A | 10/1991 | Hibino et al. |
| 5,693,091 | A | 12/1997 | Larson et al. |
| 6,529,135 | B1 | 3/2003 | Bowers et al. |
| 6,540,670 | B1 * | 4/2003 | Hirata et al. .................. 600/152 |
| 6,595,914 | B2 | 7/2003 | Kato |
| 6,810,292 | B1 | 10/2004 | Rappenecker et al. |
| 2001/0027268 | A1 | 10/2001 | Kato |
| 2003/0093103 | A1 | 5/2003 | Malackowski et al. |
| 2004/0042136 | A1 | 3/2004 | Kuo |

FOREIGN PATENT DOCUMENTS

| JP | 61-87529 | 5/1986 |
| JP | 63-174634 | 7/1988 |
| JP | 3-4831 | 1/1991 |
| JP | 3-37035 | 2/1991 |
| JP | 3-97428 | 4/1991 |
| JP | 03-097430 | 4/1991 |

(Continued)

OTHER PUBLICATIONS

Japanese Office Action dated Feb. 23, 2010.

*Primary Examiner* — Philip R Smith
(74) *Attorney, Agent, or Firm* — Scully, Scott, Murphy and Presser, P.C.

(57) ABSTRACT

An electric bending endoscope includes a temperature sensor that detects the temperature of a motor as a state value indicating the driving state of a bending drive unit. A bending control device comprises: a temperature detection unit that receives the data of the temperature detected by the temperature sensor; a record unit in which the limits of motor temperature inputted in advance are recorded; a comparison unit that compares the data of the temperature sent from the temperature detection unit with the limits of motor temperature recorded in the record unit; and a notification unit that notifies that the driving state of a motor is approaching the limit.

6 Claims, 22 Drawing Sheets

FOREIGN PATENT DOCUMENTS

| | | |
|---|---|---|
| JP | 04-304179 | 10/1992 |
| JP | 5-23298 | 2/1993 |
| JP | 5-39187 | 2/1993 |
| JP | 05-228096 | 9/1993 |
| JP | 06-217925 | 8/1994 |
| JP | 6-304123 | 11/1994 |
| JP | 08-258265 | 10/1996 |
| JP | 10-35516 | 2/1998 |
| JP | 10-174486 | 6/1998 |
| JP | 2000-210251 | 8/2000 |
| JP | 2001-275945 | 10/2001 |
| JP | 2001-346301 | 12/2001 |
| JP | 2003-500993 | 1/2003 |
| WO | WO 00/72098 A1 | 11/2000 |

* cited by examiner

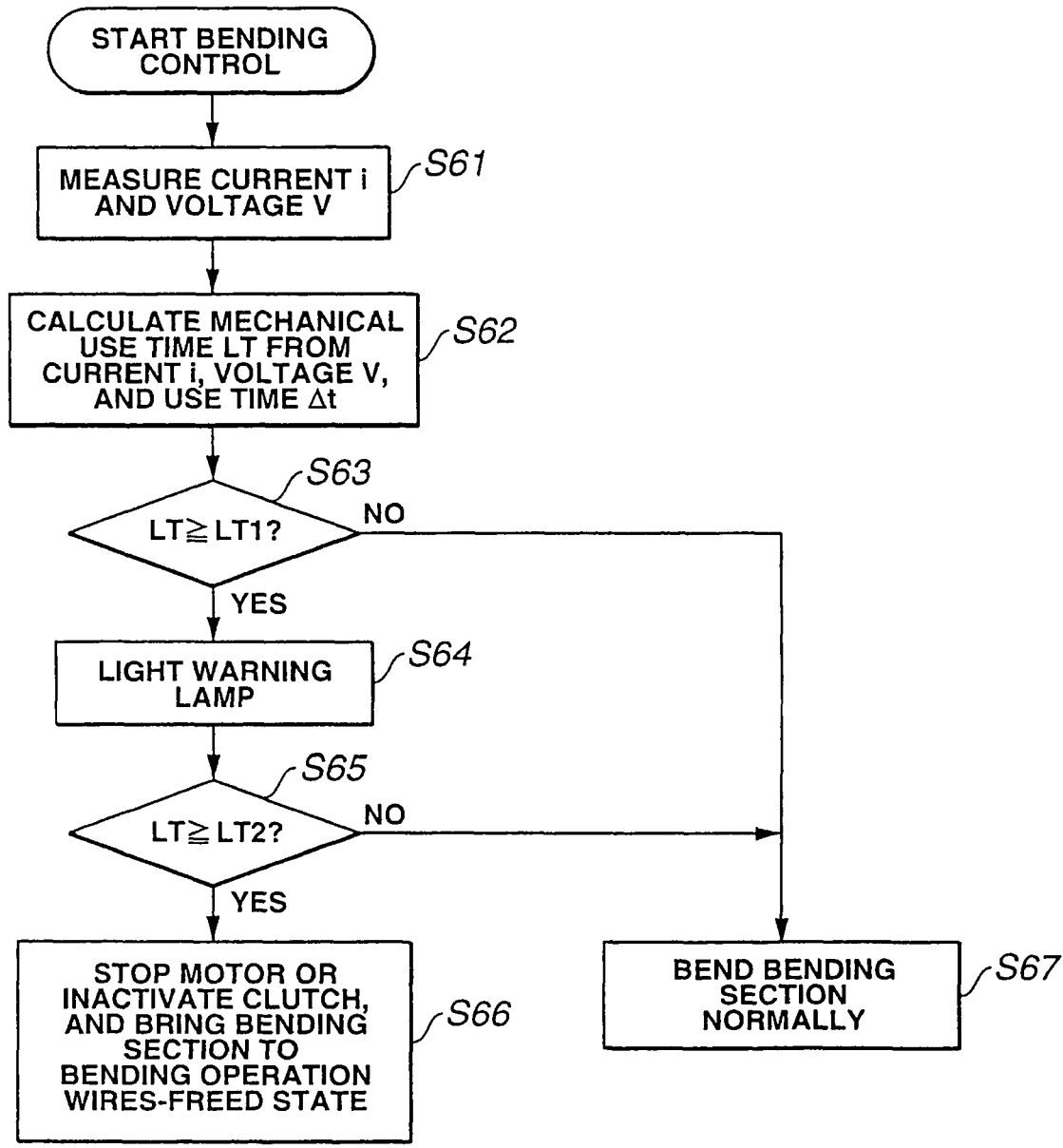

ELECTRIC BENDING ENDOSCOPE

This application, is a continuation of U.S. patent application Ser. No. 10/403,128, filed on Mar. 31, 2003 now abandoned, which claims the benefit of Japanese Application No. 2002-31429 filed in Japan on Feb. 7, 2002, the contents of which are incorporated by reference.

BACKGROUND OF THE INVENTION

1. Field of the Invention

The present invention relates to an electric bending endoscope whose bending section that adjoins a distal section of an insertion unit thereof is bent using a motor.

2. Description of the Related Art

In the past, endoscopes have been widely utilized. The endoscope has an elongated insertion unit thereof inserted into a body cavity, whereby an intracavitary organ or the like can be observed or, if necessary, various kinds of cures or treatments can be performed using a treatment instrument passed through a treatment instrument channel. Moreover, in the field of industries, the endoscope has the elongated insertion unit thereof inserted into a boiler, a turbine, an engine, a chemical plant, or the like for the purpose of observing or inspecting the internal flaws or corrosion.

The endoscope has a bending section, which can be bent freely, formed at the proximal side of a distal section of the elongated insertion unit. The endoscope has a bending operation input unit such as a bending operation lever or a joystick, or the like formed on an operating unit thereof. The bending operation input unit is handled in order to instruct or input a position to which the bending section is bent or a bending speed as a magnitude of bending. The endoscope has bending operation wires thereof mechanically drawn or released according to the instructed or input magnitude of bending. Consequently, the bending section is bent.

OBJECTS AND SUMMARY OF THE INVENTION

Accordingly, an object of the present invention is to provide an electric bending endoscope that enjoys excellent maneuverability and a long service life while suppressing unnecessary bending operation of a bending section.

Another object of the present invention is to provide an electric endoscope that notifies an operator that the service life will soon terminate and that offers excellent safety.

An electric bending endoscope in accordance with the present invention comprises: an elongated insertion unit; a bending section that adjoins a distal section of the insertion unit; a bending drive unit that drives the bending section to bend; a bending operation input unit for use in instructing bending of the bending section; a state detection unit that detects the driving state of the bending drive unit; a record unit in which the limits of abilities of the bending drive unit are recorded; a comparison unit that compares the driving state detected by the state detection unit with the limits recorded in the record unit; and a control unit that when the results of comparison sent from the comparison unit demonstrate that the driving state of the bending drive unit has reached a limit, notifies a user of the driving state of the bending drive unit.

Moreover, an electric bending endoscope in accordance with the present invention comprises: an elongated insertion unit; a bending section adjoining a distal section of the insertion unit; a bending drive unit that drives the bending section to bend; a bending operation input unit for use in instructing bending of the bending section; a state detection unit that detects the driving state of the bending drive unit; a record unit in which the limits of abilities of the bending drive unit are recorded; a comparison unit that compares the driving state detected by the state detection unit with the limits recorded in the record unit; and a control unit that when the results of comparison sent from the comparison unit demonstrate that the driving state of the bending drive unit has reached the limit, stops supply of energy to the bending drive unit.

Moreover, an electric bending endoscope in accordance with the present invention comprises: an elongated insertion unit; a bending unit adjoining a distal section of the insertion unit; a bending drive unit that drives the bending section to bend; a bending operation input unit for use in instructing bending of the bending section; a state detection unit that detects the driving state of the bending drive unit; a record unit in which the limits of abilities of the bending drive unit are recorded; a comparison unit that compares the drive state detected by the state detection unit with the limits recorded in the record unit; and a control unit that when the results of comparison sent from the comparison unit demonstrate that the driving state of the bending drive unit has reached the limit, disconnects transmission of power exerted by the bending drive unit.

Other features of the present invention and the advantages thereof will be apparent from the description made below.

BRIEF DESCRIPTION OF THE DRAWINGS

FIG. 25 is a flowchart describing bending control to be performed in the electric bending endoscope system shown in FIG. 24.

DETAILED DESCRIPTION OF THE PREFERRED EMBODIMENTS

Figure 1:
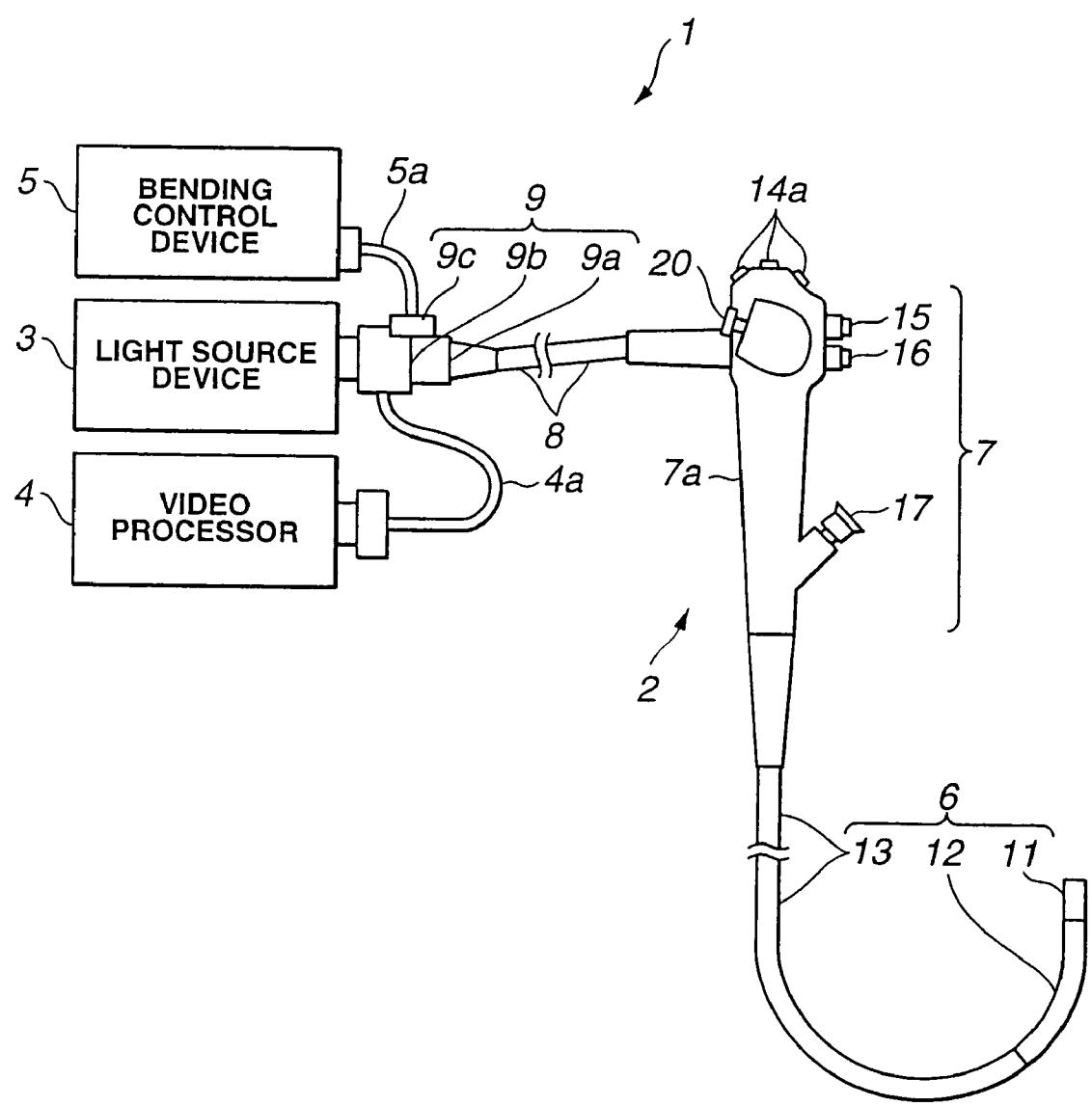
FIG. 1 shows the overall configuration of an electric bending endoscope system including a first embodiment of the present invention.

Referring to the drawings, embodiments of the present invention will be described below.

First Embodiment

FIG. 1 to FIG. 7 are explanatory diagrams concerning an electric bending endoscope in accordance with a first embodiment of the present invention.

First Embodiment

FIG. 1 to FIG. 5 are concerned with a first embodiment of the present invention.

As shown in FIG. 1, an electric bending endoscope system 1 including the first embodiment of the present invention comprises: an electric bending endoscope 2 that has a bending drive unit (see FIG. 2) which electrically bends a bending section that will be described later and that adjoins a distal section of an insertion unit; a light source device 3 that supplies illumination light to the electric bending endoscope 2; a video processor 4 that processes a signal produced by an imaging unit that will be described later and that is incorporated in the electric bending endoscope 2; and a bending control device 5 that drives and controls the bending drive unit included in the electric bending endoscope 2. The video processor 4 is connected to a monitor that is not shown, and transmits a video signal to the monitor so that an endoscopic image will be displayed.

The electric bending endoscope 2 has an operating unit 7 that is formed at the proximal end of an insertion unit 6 and that serves as a grip 7a. The electric bending endoscope 2 has a soft universal cord 8 extended from the lateral side of the operating unit 7. A light guide and signal cable which are not shown lie through the universal cord 8. A connector unit 9 is fixed to an end of the universal cord 8. The connector unit 9 includes: a light guide connector (hereinafter, LG connector) 9a that is coupled to the light source device 3 so that it can be freely decoupled; a video connector 9b which is located at the side of the LG connector 9a and into which a connection cable 4a extending from the video processor 4 is plugged so that it can be unplugged freely; and an angle connector 9c into which a connection cable 5a extending from the bending control device 5 is plugged so that it can be unplugged freely.

The endoscope insertion unit 6 (that is, the insertion unit 6 of the electric bending endoscope 2) has a hard distal section 11 that is provided at a distal part of the insertion unit, a bending section 12 that is located at the proximal end of the distal section 11 and can be bent freely, and a flexible tube 13, which is located at the proximal end of the bending section 12 and which is elongated and flexible, concatenated in that order.

The endoscope operating unit 7 (that is, the operating unit 7 of the electric bending endoscope 2) has the grip 7a, which is a region held by a user, as a proximal part thereof. The endoscope operating unit 7 has a plurality of video switches 14a, which is used to remotely control the video processor 4, arranged on the top of the grip 7a. Moreover, the endoscope operating unit 7 has an air/water button 15 that is used to supply air or water, and a suction button 16, which is used to perform suction, arranged on the lateral side thereof.

Furthermore, the endoscope operating unit 7 has a treatment instrument insertion port 17, through which a treatment instrument such as biopsy forceps are inserted, formed near the front end of the grip 7a. The treatment instrument insertion port 17 internally communicates with a treatment instrument passage channel that is not shown. A treatment instrument such as forceps that is not shown is inserted through the treatment instrument insertion port 17, and the tip of the treatment instrument passed through an internal treatment instrument passage channel is jutted out of a channel opening that is formed in the distal section 11 and a biopsy or the like can be performed.

Moreover, the endoscope operating unit 7 has a bending operation input unit 20 that is used to instruct bending of the bending section 12, such as, a joystick or a trackball.

Figure 2:
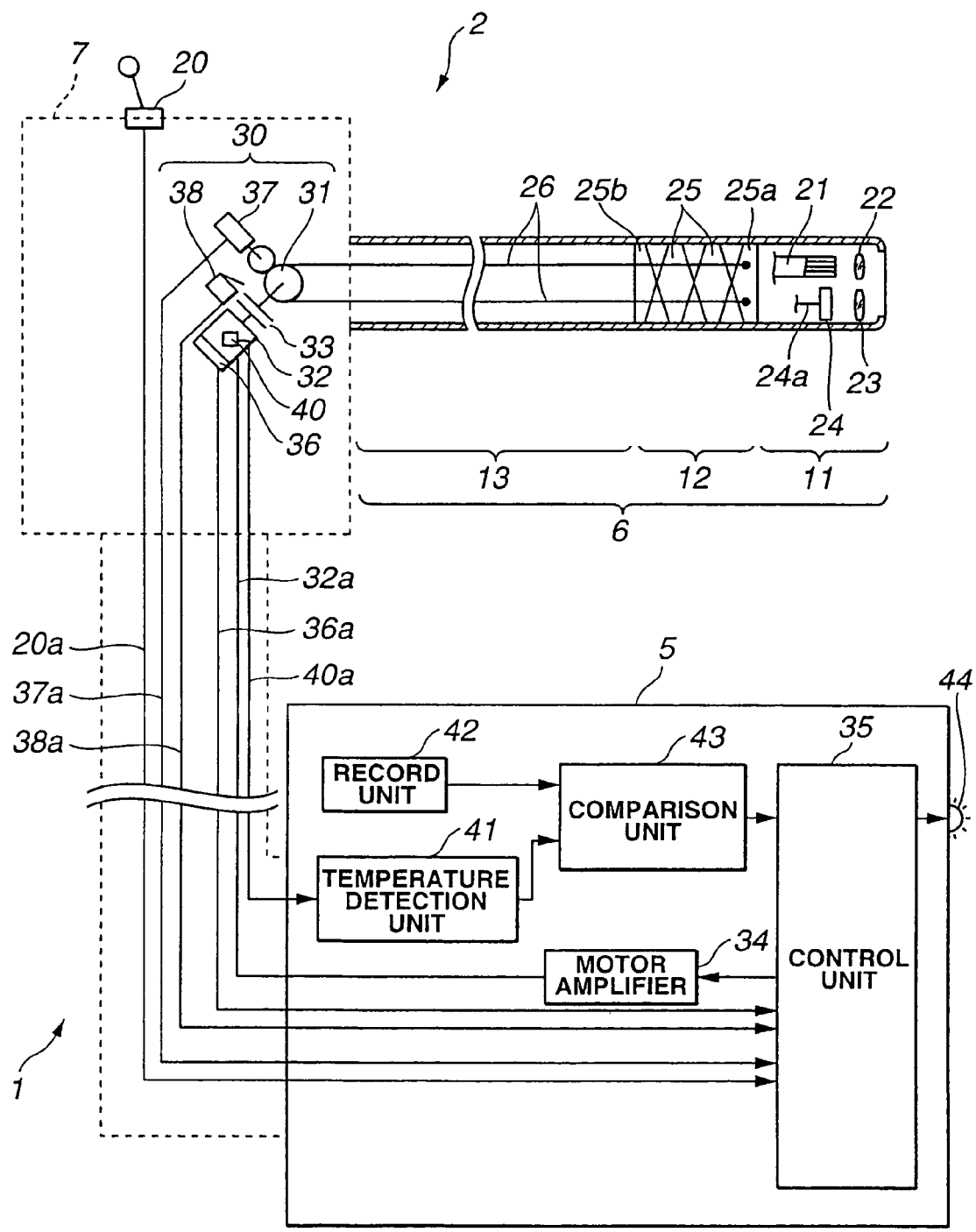
FIG. 2 shows the outline configuration of the electric bending endoscope system shown in FIG. 1.

As shown in FIG. 2, the electric bending endoscope 2 has a light guide 21, over which illumination light is propagated, passed through the insertion unit 6. The proximal end of the light guide 21 is terminated at the connector unit 9 of the universal cord 8 by way of the operating unit 7. Thus, illumination light emanating from a light source lamp, which is not shown and incorporated in the light source device 3, falls on the proximal end of the light guide 21. The illumination light propagated over the light guide 21 illuminates an object such as a lesion through a distal surface of an illumination window that is not shown and that is locked in the distal insertion unit section 11 via an illumination optical system 22.

The illuminated object has its object image captured through an observation window that is not shown and that adjoins the illumination window. The captured object image is picked up and photoelectrically converted by an imaging unit 24, which includes a charge-coupled device (CCD) or the like, via an objective optical system 23. Thus, the object image is converted into an image signal. The image signal is transmitted over a signal cable 24a extending from the imaging unit 24, and applied to the video connector 9b of the universal cord 8 via the operating unit 7. Thus, the image signal is transmitted to the video processor 4 over the connection cable 4a.

The video processor 4 processes the image signal sent from the imaging unit 24 incorporated in the electric bending endoscope 2, and produces a standard video signal so that an endoscopic image will be displayed on the monitor.

The distal insertion unit section 11 of the electric bending endoscope 2 has the leading bending piece 25a out of a plurality of bending pieces 25, which constitutes the bending section 12 and is concatenated so that the plurality of bending pieces can revolve freely, coupled to the proximal end thereof. On the other hand, the trailing bending piece 25b out of the bending pieces 25 is coupled to the distal end of the flexible tube 13.

The insertion unit 2 has bending operation wires 26, which are used to bend the bending section 12 in upward, downward, rightward, and leftward directions of a field of view for observation, passed through it. The tips of the bending operation wires 26 are respectively fixed to the leading bending piece 25a by brazing, or the like at positions of the bending section 12 associated with the upward, downward, rightward, and leftward directions. Consequently, by drawing or releasing the bending operation wires 26 associated with the directions, the bending section 12 is bent in a desired direction and the distal section 11 is angled in the desired direction.

The bending operation wires 26 are drawn or released by the bending drive unit 30, whereby the bending section 12 is electrically bent. Incidentally, FIG. 2 shows two of the bending operation wires 26 associated with the upward and downward directions or rightward and leftward directions.

The bending drive unit 30 includes a sprocket 31 that holds the proximal parts of the bending operation wires 26 while having the proximal parts wound thereabout and that draws or releases the bending operation wires 26, and a motor 32 that rotates the sprocket 31.

The bending drive unit 30 has a clutch 33, which disconnects transmission of driving force exerted by the motor 32, interposed between the sprocket 31 and motor 32. Consequently, the bending drive unit 30 can disconnect transmission of the driving force exerted by the motor 32 using the clutch 33, and establish a bending operation wires-freed state. The clutch 33 is operated under the control of a control unit that will be described later and incorporated in the bending control device 5. The clutch 33 may be designed to be operated manually.

A signal line 32a extending from the motor 32 is led to the angling connector 9c of the universal cord 8. A motor driving signal is transmitted from a motor amplifier 34 included in the bending control device 5 to the motor 32 over the connection cable 5a. The motor amplifier 34 is connected to a control unit 35 and controlled and driven by the control unit 35.

The motor 32 includes an encoder 36 that serves as a member of a rotational position detection unit so as to help detect a rotational position. A signal line 36a extending from the encoder 36 is led to the angling connector 9c of the universal cord 8. A rotational position signal indicating the detected rotational position of the motor 32 is transmitted to the control unit 35 over the signal line 36a.

The sprocket 31 converts the rotational motion of the motor 32 into the advancing or withdrawing motions of the bending operation wires 26. A potentiometer 37 that serves as a member of the rotational position detection unit so as to help detect the rotational position is connected to the sprocket 31. A signal line 37a extending from the potentiometer 37 is led to the angling connector 9c of the universal cord 8. A rotational position signal indicating the rotational position of the sprocket 31 is transmitted to the control unit 35 over the signal line 37a.

Reference numeral 38 denotes a clutch operation detecting switch 38 that detects whether the clutch 33 is activated or inactivated. A signal line 38a extending from the clutch action detecting switch 38 is led to the angling connector 9c of the universal cord 8. A clutch action signal indicating the detected action of the clutch 33 is transmitted to the control unit 35 over the signal line 38a.

Moreover, as mentioned above, the electric bending endoscope 2 has the bending operation input unit 20 such as a joystick or a trackball formed on the grip 7a of the operating unit 7. A signal line 20a extending from the bending operation input unit 20 is led to the angling connector 9c of the universal cord 8. A bending operation signal indicating an instructed bending operation is transmitted to the control unit 35 over the signal line 20a.

In response to the bending operation signal sent from the bending operation input unit 20, the control unit 35 controls the motor amplifier 34 so as to drive the motor 32 according to the signals sent from the encoder 36 and potentiometer 37 which constitute the rotational position detection unit. Thus, the control unit 35 causes the bending section 12 to bend.

Herein, when the bending section 12 of a conventional electric bending endoscope is bent over a prolonged period of time, the temperature of the motor 32 rises and the bending section 12 is driven unstably. Consequently, the bending section 12 is bent without operator's intention.

According to the present embodiment, the electric bending endoscope 2 has the driving state of the motor 32 thereof detected. The detected driving state is compared with the limits of the driving state recorded in advance. When the results of the comparison demonstrate that the driving state of the motor 32 has reached a limit, the driving state of the motor 32 is notified. Furthermore, in the present embodiment, when the results of the comparison demonstrate that the driving state of the motor 32 has reached the limit, supply of energy to the motor 32 incorporated in the electric bending endoscope 2 is stopped or transmission of power exerted by the motor 32 is disconnected.

Specifically, according to the present embodiment, the electric bending endoscope 2 includes a temperature sensor 40 that detects the temperature of the motor 32 as a state value indicating the driving state of the bending drive unit 30, such as, a thermistor or a thermocouple or the like. The bending control device 5 includes: a temperature detection unit 41 that receives temperature data produced by the temperature sensor 40; a record unit 42 in which the limits of motor temperature inputted in advance are recorded; a comparison unit 43 that compares the temperature data sent from the temperature detection unit 41 with the limits of motor temperature recorded in the record unit 42; and a notification unit 44 that notifies that the driving state of the motor 32 is approaching the limit.

The temperature sensor 40 is realized with a thermistor or a thermocouple. A signal line 40a extending from the temperature sensor 40 is led to the angling connector 9c of the universal cord 8. Temperature data is transmitted to the temperature detection unit 41 included in the bending control device 5 over the connection cable 5a.

The notification unit 44 is a warning lamp realized with an LED or the like in the present embodiment. The notification unit 44 may be a buzzer or a sound generation unit that generates an electronic sound or any other sound instead of the warning lamp. The notification unit 44 may be designed so that a message will be displayed on a monitor that is not shown.

The temperature detection unit 41 receives the data of temperature, which is detected by the temperature sensor 40, as a motor temperature t, and transmits the motor temperature t to the comparison unit 43.

In the record unit 42, a sublimit t1 immediately preceding a limit and the limit t2 that are inputted in advance are recorded as the limits of motor temperature. The recorded limits are transmitted to the comparison unit 43.

The comparison unit 43 compares the motor temperature t sent from the temperature detection unit 41 with the sublimit t1 and limit t2 read from the record unit 42, and transmits the results of comparison to the control unit 35.

The temperature detection unit 41, record unit 42, and comparison unit 43 are connected to the control unit 35, though the connections are not shown. The temperature detection unit 41, record unit 42, and comparison unit 43 are controlled based on control signals sent from the control unit 35. The temperature detection unit 41, record unit 42, and comparison unit 43 may be realized with software and installed in the control unit 35.

The control unit 35 controls, as described in the flowchart of FIG. 3 that will be referred to later, the notification unit 44 according to the results of comparison sent from the comparison unit 43. When the driving state of the motor 32 reaches the limit, the motor 32 is stopped or the bending section 12 is brought to the bending operation wires-freed state.

The electric bending endoscope 2 having the foregoing components is, as described in conjunction with FIG. 1, connected to the light source device 3, video processor 4, and bending control device 5, and used for endoscopic examination or the like.

An operator holds the grip 7a of the electric bending endoscope 2 so as to perform endoscopic examination. During the endoscopic examination, the operator handles the bending operation input unit 20 such as a joystick, or the like so as to bend the bending section 12.

The control unit 35 activates the motor amplifier 34 and reads a command (bending operation signal) inputted at the bending operation input unit 20. The control unit 35 calculates an angle of rotation of the motor from the read command (bending operation signal) sent from bending operation input unit 20. The calculated value is transmitted to the motor amplifier 34, whereby the motor amplifier 34 is informed of the angle of rotation of the motor. The motor amplifier 34 in turn drives the motor 32 so that the motor will rotate by the informed angle of rotation of the motor.

Driving force exerted by the motor 32 is conveyed to the sprocket 31 via the clutch 33, whereby the sprocket 31 rotates. The bending operation wires 26 fixed to the sprocket 31 are drawn or released. This causes the bending section 12 to bend in a predetermined manner.

Herein, when the bending section 12 of the electric bending endoscope 2 is bent over a prolonged period of time, the temperature of the motor 32 rises. At this time, the electric bending endoscope 2 has the bending of the bending section 12 thereof controlled as described in the flowchart of FIG. 3.

Figure 3:
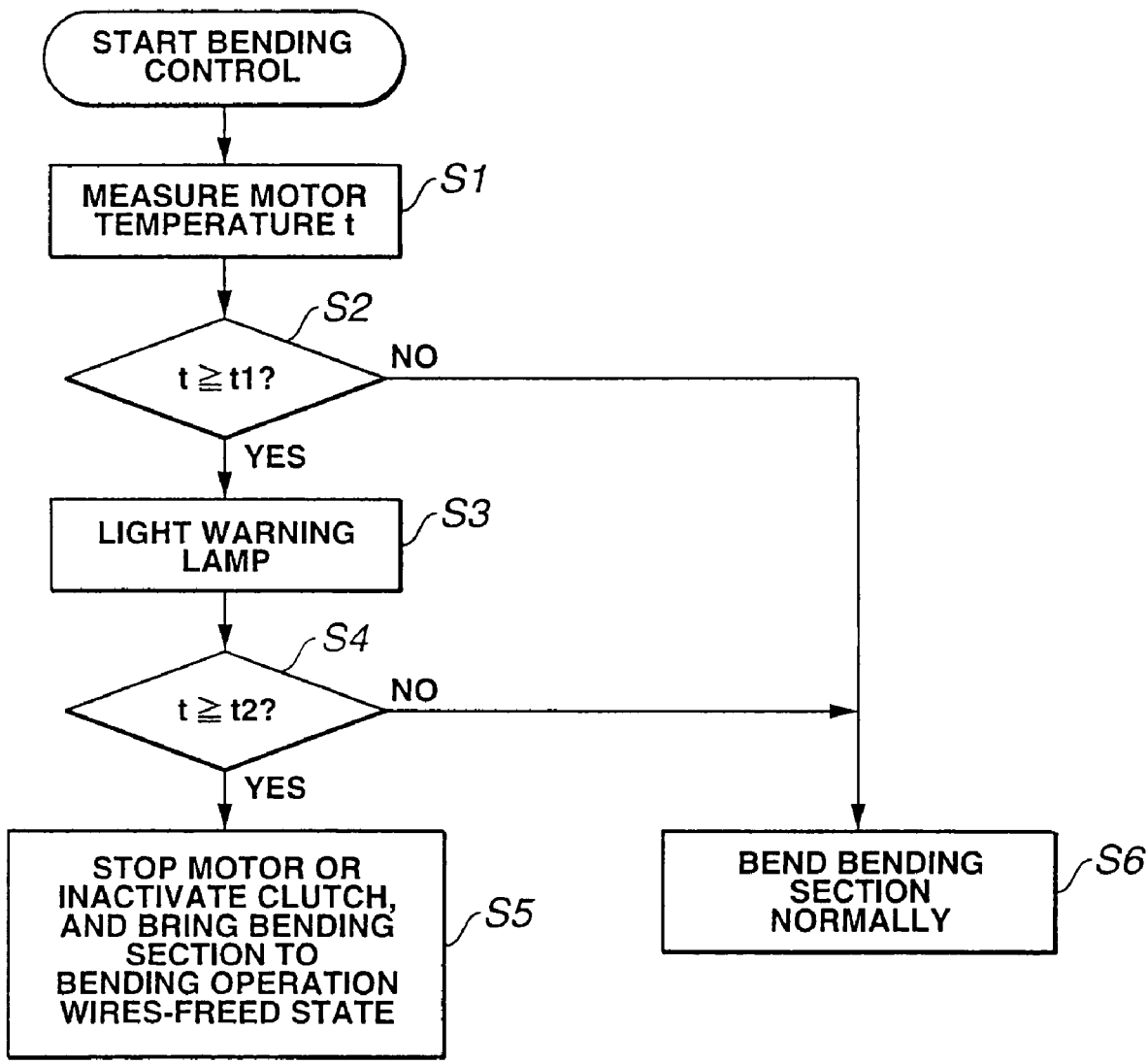
FIG. 3 is a flowchart describing bending control performed in the endoscope system shown in FIG. 2.

As described in FIG. 3, first, the temperature sensor 40 measures or detects the temperature of the motor 32 (step S1), and transmits the data of the detected temperature of the motor 32 to the temperature detection unit 41 included in the bending control device 5. The temperature detection unit 41 in turn receives the temperature data sent from the temperature sensor 40 as a motor temperature t, and transmits the motor temperature t to the comparison unit 43 in response to an output signal of the control unit 35.

On the other hand, the record unit 42 transmits the sublimit t1 and the limit t2 of motor temperature, which are recorded, to the comparison unit 43 in response to the output signal of the control unit 35. The comparison unit 43 compares the motor temperature t sent from the temperature detection unit 41 with the sublimit t1 and limit t2 read from the record unit 42, and transmits the results of comparison to the control unit 35.

Based on the results of comparison sent from the comparison unit 43, the control unit 35 determines whether the motor temperature t has reached the sublimit t1 (step S2). When the control unit 35 determines that the motor temperature t has reached the sublimit t1, the control unit 35 transmits a lighting signal so as to light the warning lamp (step S3). Consequently, the control unit 35 notifies that the driving state of the motor 32 is approaching the limit.

Furthermore, the control unit 35 determines whether the motor temperature t has reached the limit t2 (step S4). When the control unit 35 determines that the motor temperature t has reached the limit t2, the control unit 35 transmits a motor stop signal to the motor amplifier 34 so as to stop the motor 32. Otherwise, the control unit 35 transmits a clutch off signal so as to inactivate the clutch, and brings the bending section 12 to the bending operation wires-freed state (step S5). Consequently, when the driving state of the motor 32 reaches the limit, the control unit 35 does not permit transmission of driving force exerted by the motor 32 to the sprocket 31. Therefore, the bending section 12 will not be bent without operator's intention.

On the other hand, when the results of comparison sent from the comparison unit 43 demonstrate that the motor temperature t is equal to or smaller than the sublimit t1 or ranges from the sublimit t1 to the limit t2, the control unit 35 extends control so that the bending section 12 will be bent normally (step S6).

Consequently, the temperature of the motor 32 included in the electric bending endoscope 2 of the present embodiment is detected and compared with the limits recorded in advance. When the motor temperature reaches the sublimit, the fact is notified. Moreover, when the motor temperature reaches the limit, supply of energy to the motor 32 is stopped or transmission of power exerted by the motor 32 is disconnected.

Consequently, the unnecessary bending of the bending section 12 of the electric bending endoscope 2 of the present embodiment can be suppressed. The maneuverability of the bending section 12 can be improved and the service life thereof can be extended.

Figure 4:
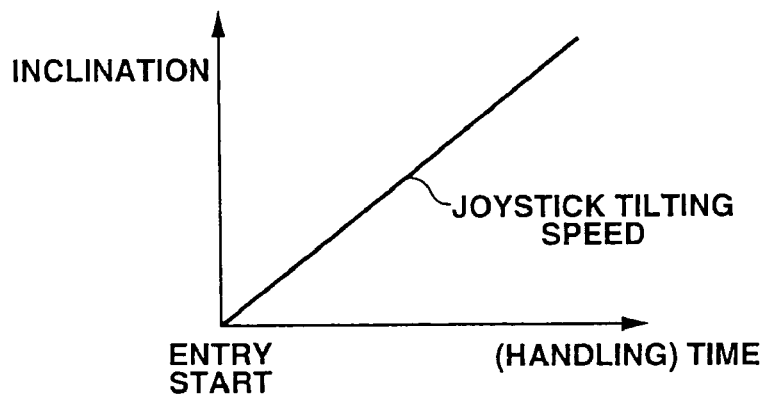
FIG. 4 is a graph indicating a joystick tilting speed calculated based on the (handling) time during which a joystick is handled and an inclination.

When the bending operation input unit 20 is realized with a joystick, the control unit 35 included in the bending control device 5 can calculate, as seen from the graph of FIG. 4, a joystick tilting speed from the inclination angle of the joystick and the (handling) time thereof.

Figure 5:
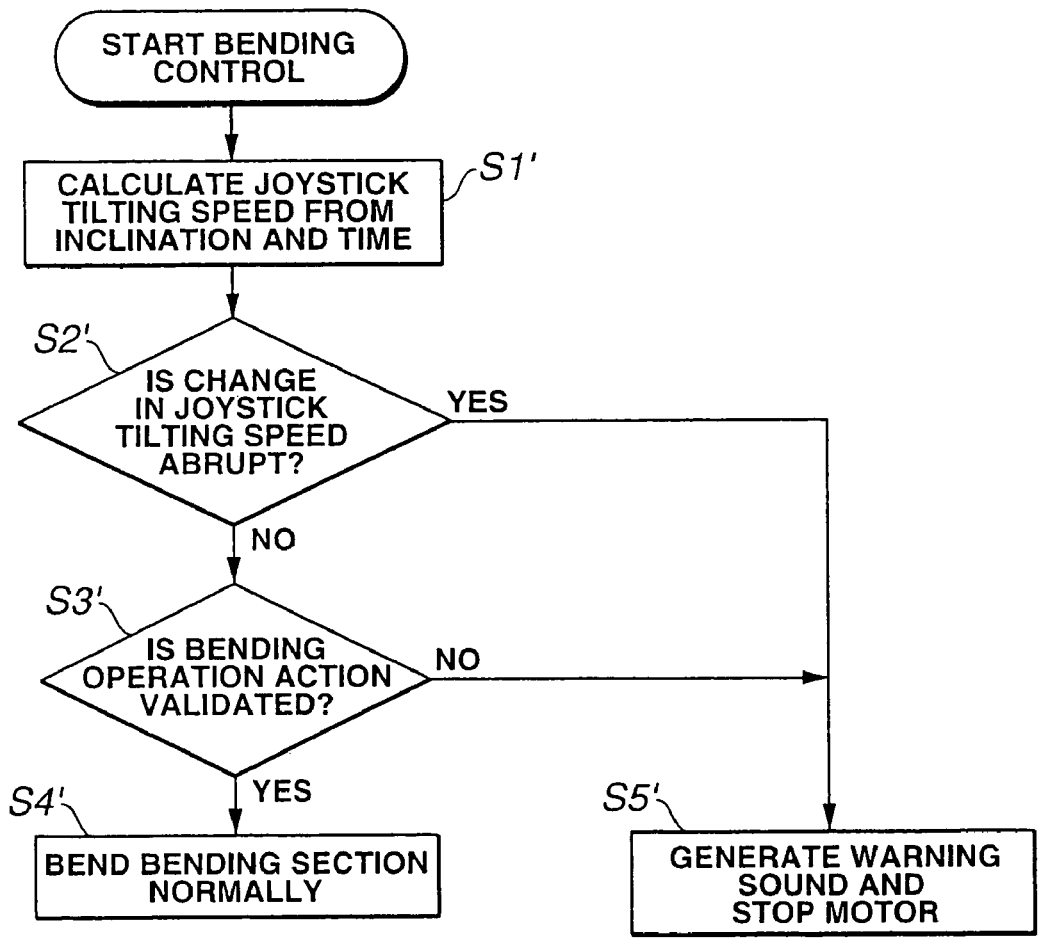
FIG. 5 is a flowchart describing bending control based on the calculation whose results are graphically shown in FIG. 4.

Control may be extended as described in the flowchart of FIG. 5.

As described in FIG. 5, the control unit 35 included in the bending control device calculates the joystick tilting speed from the inclination of the joystick and the time (step S1').

Thereafter, the control unit 35 determines based on the result of calculation whether a change in the joystick tilting speed is made in an abrupt manner (step S2'). When the calculated value is equal to or larger than a pre-set predetermined value, the control unit 35 determines whether a change in the joystick tilting speed is made in an abrupt manner.

When the control unit 35 determines that a change in the joystick tilting speed is not made in an abrupt manner, the control unit 35 determines based on a detection signal sent from an intention sensor 39 whether a bending operation action instructed by handling the joystick is validated (step S3').

When a bending operation action instructed by handling the joystick is validated, the control unit 35 extends control so that the bending section 12 will be bent normally (step S4').

On the other hand, when the control unit 35 determines that a bending operation action instructed by handling the joystick is invalidated or that a change in the joystick tilting speed is made in an abrupt manner, the control unit 35 generates a warning sound. Moreover, the control unit 35 inactivates the motor amplifier 34 so as to stop the motor 32 (step S5').

The bending section 12 of the electric bending endoscope 2 can be bent as mentioned above.

Consequently, bending the bending section 12 of the electric bending endoscope 2 of this variant without operator's intention can be prevented.

The electric bending endoscope 2 of the present embodiment has the present invention adapted to an electronic endoscope having the imaging device 24, which picks up a received object image, incorporated in the distal insertion unit section 11. The present invention is not limited to the electronic endoscope. Needless to say, the present invention may be adapted to an optical endoscope that includes an image transmission unit which conveys a received object image. Herein, the object image conveyed by the image transmission unit can be viewed through an eyepiece unit located at the rear end of an operating unit.

Moreover, the electric bending endoscope 2 of the present embodiment is detachably connected to the bending control device 5. The bending control device 5 drives or controls the bending drive unit 30. The present invention is not limited to this mode. Alternatively, the bending control device 5 may be incorporated in the electric bending endoscope 2.

Second Embodiment

Figure 6:
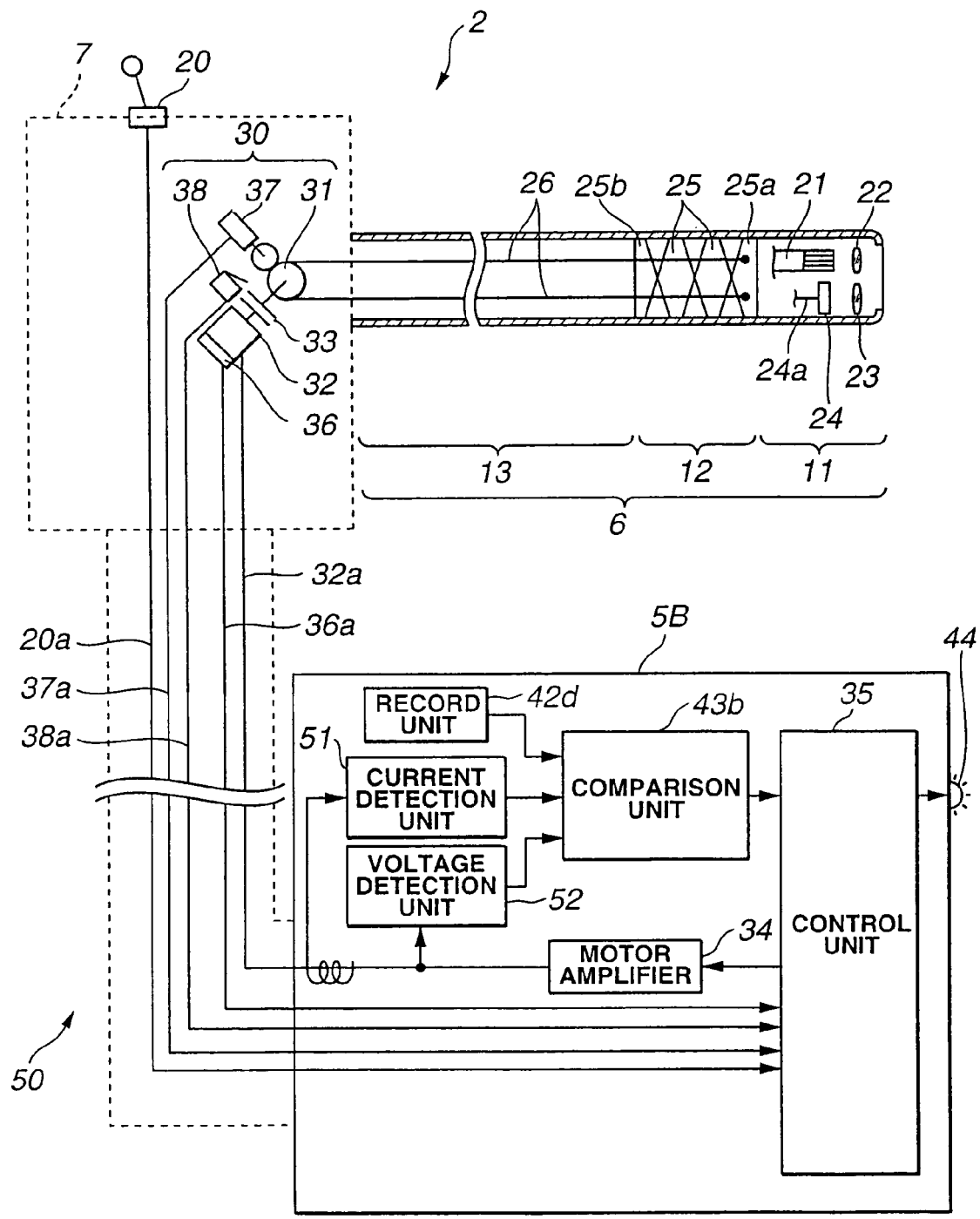
FIG. 6 shows the outline configuration of an electric bending endoscope system including a second embodiment of the present invention.
Figure 7:
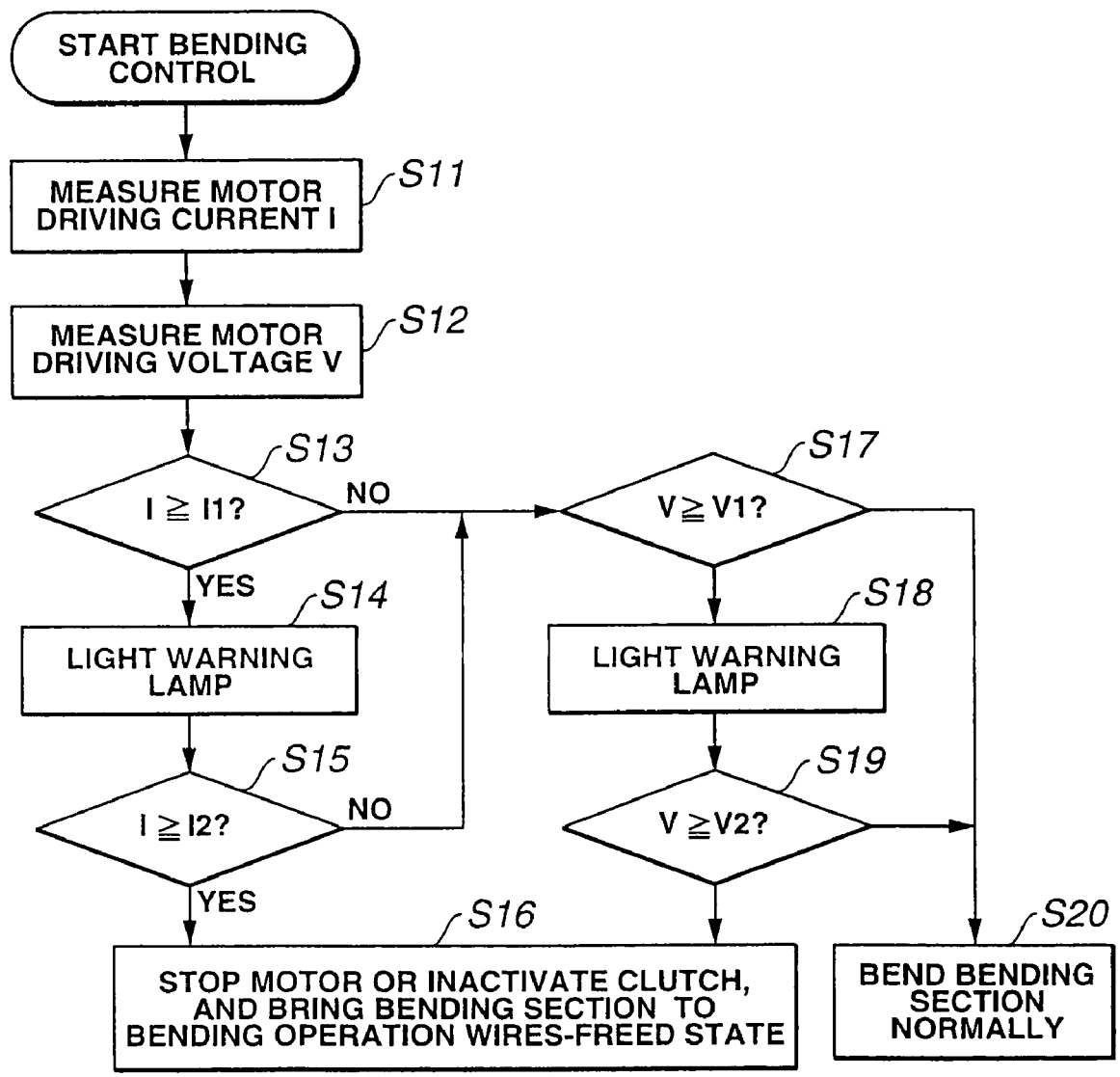
FIG. 7 is a flowchart describing bending control performed in the electric bending endoscope system shown in FIG. 6.

FIG. 6 and FIG. 7 are concerned with a second embodiment of the present invention.

According to the first embodiment, the temperature of the motor 32 is detected as a state value indicating the driving state of the bending drive unit 30, and compared with recorded limits. According to the second embodiment, a current and a voltage serving as a motor driving signal are detected as state values indicating the driving state of the bending drive unit 30, and compared with the recorded limits. The other constituent features are identical to those of the first embodiment. The description of the constituent features will be omitted. Moreover, components identical to those of the first embodiment will be described with the same reference numerals assigned thereto.

As shown in FIG. 6, an electric bending endoscope system 50 including the second embodiment of the present invention is configured so that a current and a voltage serving as a motor driving signal will be detected as state values indicating the driving state of the bending drive unit 30, and compared with recorded limits.

To be more specific, a bending control device 5B includes: a current detection unit 51 that detects a current serving as a motor driving signal, which is transmitted from the motor amplifier 34, as a state value indicating the driving state of the bending drive unit 30 included in the electric bending endoscope 2; a voltage detection unit 52 that detects a voltage serving as the motor driving signal; a record unit 42b in which the limits of the current and voltage serving as the motor driving signal which are inputted in advance are recorded; a comparison unit 43b that compares the data items of the current and voltage, which are detected by the current detection unit 51 and voltage detection unit 52 respectively, with the limits of the current and voltage recorded in the record unit 42b.

The current detection unit 51 receives the current data detected over the signal line 32a as a motor driving current I, and transmits the motor driving current I to the comparison unit 43b. Noted is that the motor driving current I is a state value proportional to the torque exerted by the motor. The voltage detection unit 52 receives the voltage data, which is detected over the signal line 32a, as a motor driving voltage V, and transmits the motor driving voltage V to the comparison unit 43b. Noted is that the motor driving voltage V is a state value proportional to the rotating speed of the motor.

In the record unit 42b, a sublimit I1 immediately preceding a limit and the limit I2 which are inputted in advance are recorded as the limits of the motor driving current, and a sublimit V1 immediately preceding a limit and the limit V2 which are inputted in advance are recorded as the limits of the motor driving voltage. The recorded limits are transmitted to the comparison unit 43b.

The comparison unit 43b compares the motor driving voltage V sent from the current detection unit 51 with the sublimit I1 and limit I2 read from the record unit 42b, and then transmits the results of the comparison to the control unit 35. The comparison unit 43b then compares the motor driving voltage V sent from the voltage detection unit 52 with the sublimit V1 and limit V2 read from the record unit 42b, and then transmits the results of the comparison to the control unit 35.

The current detection unit 51, voltage detection unit 52, record unit 42b, and comparison unit 43b are connected to the control unit 35, though the connections are not shown. The current detection unit 51, voltage detection unit 52, record unit 42b, and comparison unit 43b are controlled with control signals sent from the control unit 35. Incidentally, the current detection unit 51, voltage detection unit 52, record unit 42b, and comparison unit 43b may be realized with software and installed in the control unit 35.

The control unit 35 controls, as described in the flowchart of FIG. 7, the notification unit 44 according to the results of the comparisons sent from the comparison unit 43b. When the driving state of the motor 32 reaches the limit, the control unit 35 stops the motor 32 or brings the bending section 12 to the bending operation wires-freed state.

The electric bending endoscope 2 thus configured is, similarly to the one described in relation to the first embodiment, connected to the light source device 3, video processor 4, and bending control device 5B, and used for endoscopic examination or the like.

An operator holds the grip 7a of the electric bending endoscope 2 so as to perform endoscopic examination. During the endoscopic examination, the operator handles the bending operation input unit 20 such as a joystick, or the like so as to bend the bending section 12.

When the bending section 12 of the electric bending endoscope 2 is bent over a prolonged period of time, the motor driving signal sent from the motor amplifier 34 to the motor 32 rises. At this time, the electric bending endoscope 2 has the bending of the bending section 12 thereof controlled as described in the flowchart of FIG. 7.

As shown in FIG. 7, first, the current detection unit 51 measures or detects the motor driving current I (step S11). In response to an output signal of the control unit 35, the current detection unit 51 transmits the detected motor driving current I to the comparison unit 43. At the same time, the voltage detection unit 52 measures or detects the motor driving voltage V (step S12), and transmits the detected motor driving voltage V to the comparison unit 43 in response to the output signal of the control unit 35.

On the other hand, from the record unit 42b, the sublimit I1 immediately preceding the limit of the motor driving current and the limit I2, which are recorded in the record unit 42b, are transmitted in response to an output signal of the control unit 35. Moreover, the sublimit V1 immediately preceding the limit of the motor driving voltage and the limit V2 are transmitted to the comparison unit 43b.

The comparison unit 43b compares the motor driving current I sent from the current detection unit 51 with the sublimit I1 and limit I2 read from the record unit 42, and transmits the results of the comparison to the control unit 35. Moreover, the comparison unit 43b compares the motor driving voltage V-sent from the voltage detection unit 52 with the sublimit V1 and limit V2 read from the record unit 42b, and transmits the results of the comparison to the control unit 35.

The control unit 35 determines based on the results of comparison sent from the comparison unit 43b whether the motor driving current I has reached the sublimit I1 (step S13). When the control unit 35 determines that the motor driving current I has reached the sublimit I1, the control unit 35 transmits a lighting signal so as to light the warning lamp (step S14). Thus, the control unit 35 notifies that the driving state of the motor 32 is approaching a state in which the motor 32 exerts an excessive torque.

Furthermore, the control unit 35 determines whether the motor driving current I has reached the limit I2 (step S15). When the control unit 35 determines that the motor driving current I has reached the limit I2, the control unit 35 stops the motor 32 or inactivates the clutch so as to bring the bending section 12 to the bending operation wires-freed state (step S16) in the same manner as the one described in relation to the first embodiment. Consequently, when the driving state of the motor 32 reaches the state in which the motor 32 exerts an excessive torque, the control unit 35 does not permit transmission of driving force exerted by the motor 32 to the sprocket 31.

On the other hand, when the motor driving current I is equal to or smaller than the sublimit I1 or ranges from the sublimit I1 to the limit I2, the control unit 35 switches to the results of comparison of the motor driving voltage V.

The control unit 35 determines whether the motor driving voltage V has reached the sublimit V1 (step S17). When control unit 35 determines that the motor driving voltage V has reached the sublimit V1, the control unit 35 transmits a lighting signal so as to light the warning lamp (step S18). Consequently, the control unit 35 notifies that the driving state of the motor 32 is approaching a state in which the motor 32 exhibits an excessive rotating speed.

Furthermore, the control unit 35 determines whether the motor driving voltage V has reached the limit V2 (step S19). When the control unit 35 determines that the motor driving voltage V has reached the limit V2, the control unit stops the motor 32 or inactivates the clutch so as to bring the bending section 12 to the bending operation wires-freed state in the same manner as described in relation to the driving current I (step S16). Consequently, when the driving state of the motor 32 reaches the state in which the motor 32 exhibits an excessive rotating speed, the control unit 35 does not permit transmission of driving force exerted by the motor 32 to the sprocket 31.

On the other hand, when the results of comparison sent from the comparison unit 43b demonstrate that the motor driving current I is equal to or smaller than the sublimit I1 or ranges from the sublimit I1 to the limit I2, and that the motor driving voltage V is equal to or smaller than the sublimit V1 or ranges from the sublimit V1 to the limit V2, the control unit 35 extends control so that the bending section 12 will be bent normally (step S20).

Consequently, the motor driving signal applied to the motor 32 included in the electric bending endoscope 2 in accordance with the second embodiment is detected and compared with the pre-recorded limits. When the motor driving signal reaches the sublimit, the fact is notified. When the motor driving signal reaches the limit, supply of energy to the motor 32 is stopped or transmission of power exerted by the motor 32 is disconnected.

Consequently, the electric bending endoscope 2 in accordance with the second embodiment provides the same advantage as the first embodiment does.

Third Embodiment

FIG. 8 to FIG. 14 are concerned with a third embodiment of the present invention.

According to the first and second embodiments, the driving state of the motor 32 is detected as a state value indicating the driving state of the bending drive unit 30, and compared with the recorded limits. According to the third embodiment, the rotational position or rotating speed of the sprocket 31 is detected as the state value indicating the driving state of the bending drive unit 30, and compared with recorded limits. The other constituent features are identical to those of the first embodiment. The description of the constituent features will be omitted. The components identical to those of the first embodiment will be described with the same reference numerals assigned thereto.

Figure 8:
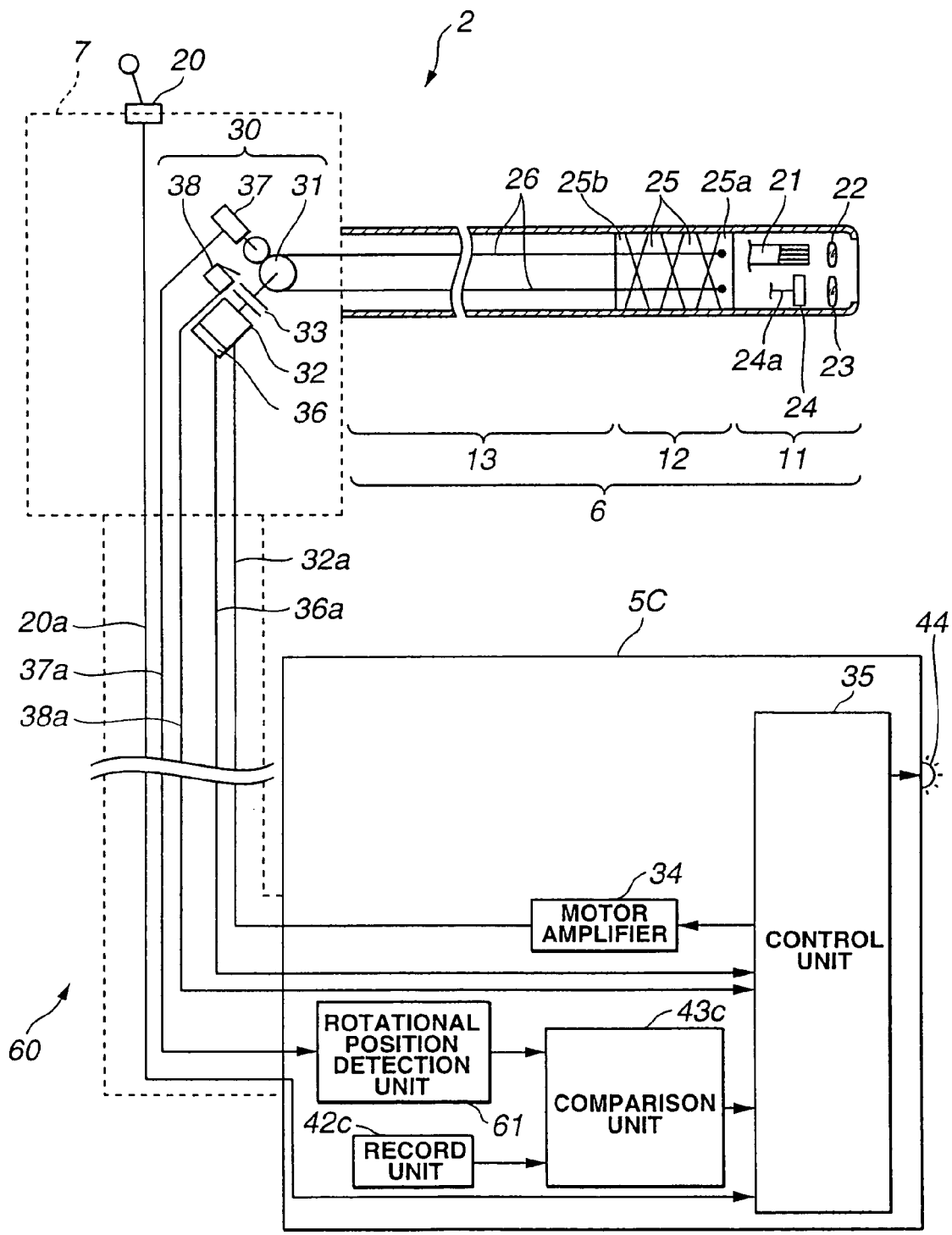
FIG. 8 shows the outline configuration of an electric bending endoscope system including a third embodiment of the present invention.

As shown in FIG. 8, an electric bending endoscope system 60 including the third embodiment is configured so that the rotational position of the sprocket 31 will be detected as a state value indicating the driving state of the bending drive unit 30, and compared with recorded limits.

To be more specific, a bending control device 5C comprises: a rotational position-of-sprocket detection unit (hereinafter, a rotational position detection unit) 61 that detects the rotational position of the sprocket as a state value, which indicates the driving state of the bending drive unit 30 included in the electric bending endoscope 2, from a rotational position signal sent from the potentiometer 37; a record unit 42c in which the limits of the rotational position of the sprocket that are inputted in advance are recorded; and a comparison unit 43c that compares the data of the rotational position of the sprocket detected by the rotational position detection unit 61 with the limits of the rotational position of the sprocket recorded in the record unit 42c.

The rotational position detection unit 61 acquires the data of the rotational position of the sprocket from the rotational position signal sent from the potentiometer 37, thus receives the rotational position P of the sprocket, and transmits the rotational position P of the sprocket to the comparison unit 43c. The rotational position P of the sprocket is a state value equivalent to the one indicating a position to which the bending section 12 is bent. Moreover, the rotational position P of the sprocket may be received from the encoder 36.

In the record unit 42c, a sublimit P1 immediately preceding a limit and the limit P2 that are inputted in advance are recorded as the limits of the rotational position of the sprocket. The recorded limits are transmitted to the comparison unit 43c.

The comparison unit 43c compares the rotational position P of the sprocket sent from the rotational position detection unit 61 with the sublimit P1 and limit P2 read from the record unit 42c, and transmits the results of the comparison to the control unit 35.

The rotational position detection unit 61, record unit 42c, and comparison unit 43c are connected to the control unit 35, though the connections are not shown. The rotational position detection unit 61, record unit 42c, and comparison unit 43c are controlled with control signals sent from the control unit 35. Incidentally, the rotational position detection unit 61, record unit 42c, and comparison unit 43c may be realized with software and installed in the control unit 35.

The control unit 35 controls, as described in the flowchart of FIG. 9 which will be referred to later, the notification unit 44 according to the results of comparison sent from the comparison unit 43c. When the driving state of the motor 32 reaches the limit, the control unit 35 stops the motor 32 or brings the bending section 12 to the bending operation wires-freed state.

The electric bending endoscope 2 is, similarly to the one described in relation to the first embodiment, connected to the light source device 3, video processor 4, and bending control device 5C, and used for endoscopic examination or the like.

An operator holds the grip 7a of the electric bending endoscope 2 so as to perform endoscopic examination. During the endoscopic examination, the operator handles the bending operation input unit 20 such as a joystick, or the like so as to bend the bending section 12.

When the bending section 12 of the electric bending endoscope 2 is bent over a prolonged period of time, the driving state of the motor 32 reaches the limit. Consequently, the sprocket 37 exerts excessive bending force, and the rotational position P of the sprocket rises. At this time, the electric bending endoscope 2 has the bending of the bending section 12 thereof controlled as described in the flowchart of FIG. 9.

Figure 9:
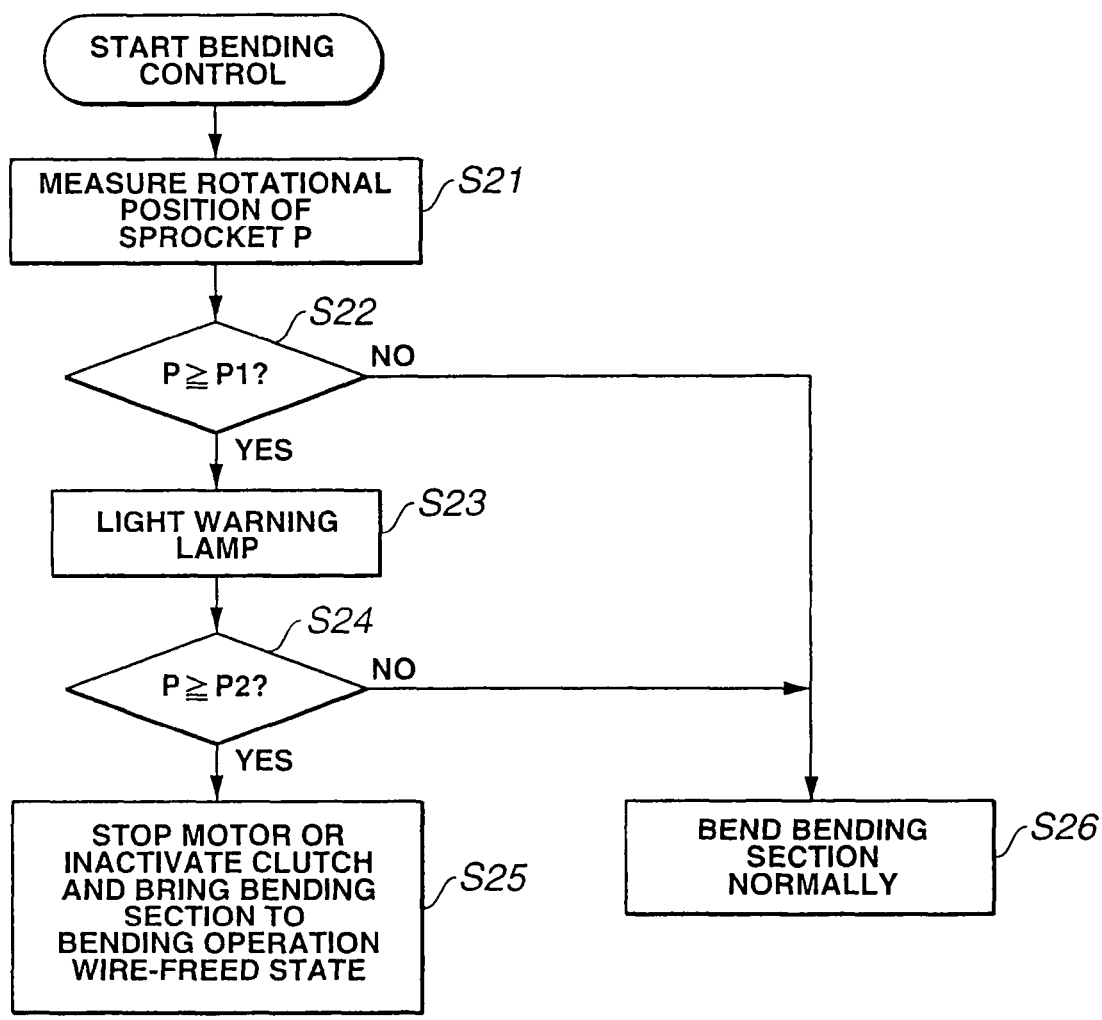
FIG. 9 is a flowchart describing bending control performed in the electric bending endoscope system shown in FIG. 8.

As described in FIG. 9, the rotational position detection unit 61 measures or detects the data of the rotational position of the sprocket from the rotational position signal sent from the potentiometer 37, and thus receives the rotational position P of the sprocket (step S21). In response to an output signal sent from the control unit 35, the rotational position detection unit 61 transmits the detected rotational position P of the sprocket to the comparison unit 43c.

On the other hand, from the record unit 42c, the recorded sublimit P1 and limit P2 of the rotational position of the sprocket are transmitted to the comparison unit 43c in response to an output signal sent from the control unit 35.

The comparison unit 43c compares the rotational position P of the sprocket sent from the rotational position detection unit 61 with the sublimit P1 and limit P2 read from the record unit 42c, and transmits the results of the comparison to the control unit 35.

The control unit 35 determines based on the results of comparison sent from the comparison unit 43c whether the rotational position P of the sprocket has reached the sublimit P1 (step S22). When the control unit 35 determines that the rotational position P of the sprocket has reached the sublimit P1, the control unit 35 transmits a lighting signal so as to light the warning lamp (step S23). Thus, the control unit 35 notifies that the driving state of the motor 32 is approaching the limit and the sprocket 37 is beginning to exert excessive bending force.

Furthermore, the control unit 35 determines whether the rotational position P of the sprocket has reached the limit P2 (step S24). When the control unit 35 determines that the rotational position P of the sprocket has reached the limit P2, the control unit 35 stops the motor 32 or inactivates the clutch so as to bring the bending section 12 to the bending operation wires-freed state (step S25) in the same manner as described in relation to the first embodiment. Thus, when the driving state of the motor 32 reaches the limit and the sprocket 37 exerts excessive bending force, the control unit 35 does not permit transmission of driving force exerted by the motor 32 to the sprocket 31.

On the other hand, when the results of comparison sent from the comparison unit 43c demonstrate that the rotational position P of the sprocket is equal to or smaller than the sublimit P1 or ranges from the sublimit P1 to the limit P2, the control unit 35 extends control so that the bending section 12 will be bent normally (step S26).

Consequently, the rotational position of the sprocket 31 incorporated in the electric bending endoscope 2 in accordance with the third embodiment is detected and compared with the pre-recorded limits. When the rotational position of the sprocket reaches the sublimit, the fact is notified. When the rotational position of the sprocket reaches the limit, supply of energy to the motor 32 is stopped or transmission of power exerted by the motor 32 is disconnected.

Consequently, the electric bending endoscope 2 in accordance with the third embodiment provides the same advantage as the first embodiment does.

Alternatively, the rotating speed of the sprocket 31 incorporated in the electric bending endoscope may be detected as a state value indicating the driving state of the bending drive unit 30 and compared with recorded limits.

Figure 10:
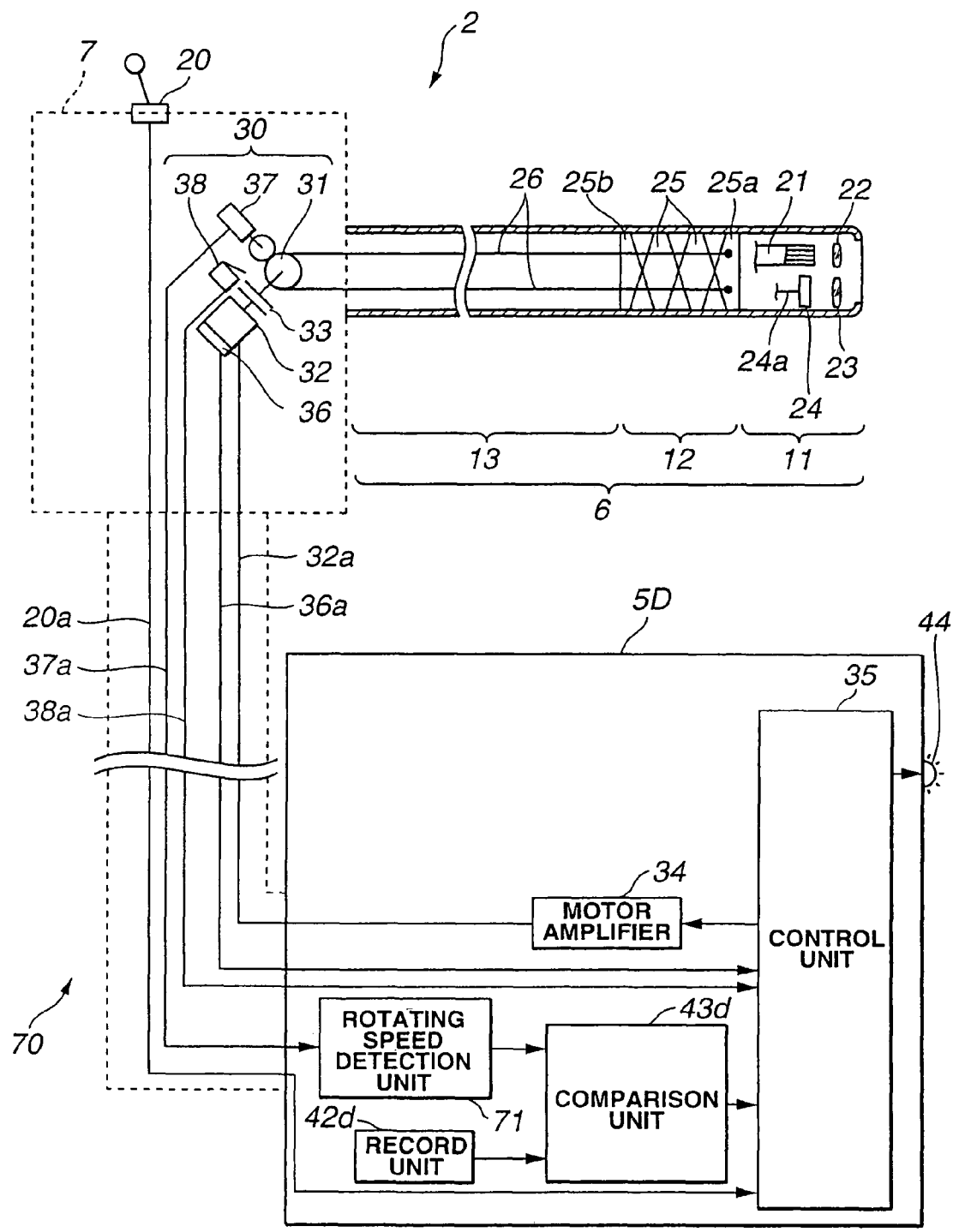
FIG. 10 shows the outline configuration of a variant of the electric bending endoscope system shown in FIG. 8.

Specifically, an electric bending endoscope system 70 is, as shown in FIG. 10, configured so that the rotating speed of the sprocket 31 will be detected as the state value indicating the driving state of the bending drive unit 30 and compared with a recorded range of limits.

To be more specific, a bending control device 5D comprises: a rotating speed-of-sprocket detection unit (hereinafter, a rotating speed detection unit) 71 that detects the rotating speed of the sprocket as a state value, which indicates the driving state of the bending drive unit 30 included in the electric bending endoscope 2, from a rotating position signal sent from the potentiometer 37; a record unit 42d in which the limits of the rotating speed of the sprocket that are inputted in advance are recorded; and a comparison unit 43d that compares the data of the rotating speed of the sprocket detected by the rotating speed detection unit 71 with the limits of the rotating speed of the sprocket recorded in the record unit 42d.

The rotating speed detection unit 71 acquires the data of the rotational position of the sprocket from the rotational position signal sent from the potentiometer 37, and thus receives the rotational position P of the sprocket. The rotating speed detection unit 71 then calculates the time derivative of the rotational position P of the sprocket so as to work out a rotating speed V of the sprocket, and then transmits the rotating speed V of the sprocket to the comparison unit 43d. The rotating speed V of the sprocket is a state value equivalent to the one indicating the bending speed of the bending section 12. Moreover, the rotational position P of the sprocket may be received from the encoder 36.

In the record unit 42d, a sublimit V1 immediately preceding a limit and the limit V2 that are inputted in advance are recorded as the limits of the rotating speed of the sprocket. The recorded limits are transmitted to the comparison unit 43d.

The comparison unit 43d compares the rotating speed V of the sprocket sent from the rotating speed detection unit 71 with the sublimit V1 and limit V2 read from the record unit 42d, and transmits the results of the comparison to a control unit 35.

The rotating speed detection unit 71, record unit 42d, and comparison unit 43d are connected to the control unit 35, though the connections are not shown. The rotating speed detection unit 71, record unit 42d, and comparison unit 43d are controlled with control signals sent from the control unit 35. Incidentally, the rotating speed detection unit 71, record unit 42d, and comparison unit 43d may be realized with software and installed in the control unit 35.

The control unit 35 controls, as described in the flowchart of FIG. 11 that will be referred to later, the notification unit 44 according to the results of comparison sent from the comparison unit 43d. When the rotating speed of the sprocket reaches the limit, the control unit 35 stops the motor 32 or brings the bending section 12 to the bending operation wires-freed state.

The electric bending endoscope 2 is, similarly to the one described in relation to the first embodiment, connected to the light source device 3, video processor 4, and bending control device 5D, and used for endoscopic examination or the like.

An operator holds the grip 7a of the electric bending endoscope 2 so as to perform endoscopic examination. During the endoscopic examination, the operator handles the bending operation input unit 20 such as a joystick, or the like so as to bend the bending section 12.

Herein, when the bending section 12 of the electric bending endoscope 2 is bend over a prolonged period of time, the driving state of the motor 32 reaches the limit. The sprocket 37 exerts excessive bending force and the rotating speed V of the sprocket rises. At this time, the electric bending endoscope 2 has the bending of the bending section 12 thereof controlled as described in the flowchart of FIG. 11.

Figure 11:
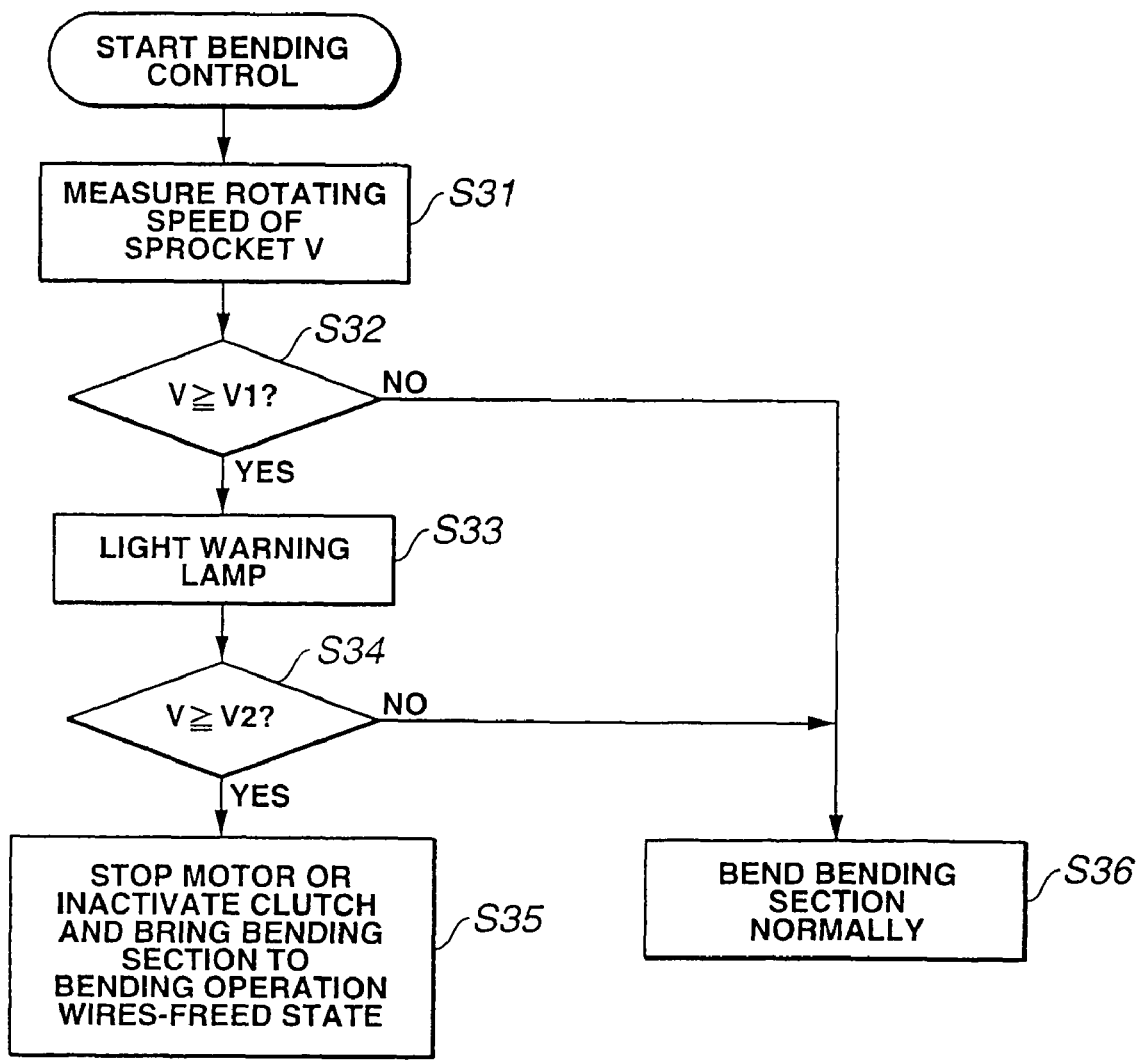
FIG. 11 is a flowchart describing bending control performed in the electric bending endoscope system shown in FIG. 10.

As described in FIG. 11, the rotating speed detection unit 71 acquires the data of the rotating speed of the sprocket from a rotating position signal sent from the potentiometer 37, and thus measures or detects the rotating speed V of the sprocket (step S31). In response to an output signal sent from the control unit 35, the rotating speed detection unit 71 transmits the detected rotating speed V of the sprocket to the comparison unit 43d.

On the other hand, from the record unit 42d, the recorded sublimit V1 and limit V2 of the rotating speed of the sprocket are transmitted to the comparison unit 43d in response to an output signal sent from the control unit 35.

The comparison unit 43d compares the rotating speed V of the sprocket sent from the rotating speed detection unit 71 with the sublimit V1 and limit V2 read from the record unit 42d, and transmits the results of the comparison to the control unit 35.

The control unit 35 determines based on the results of comparison sent from the comparison unit 43d whether the rotating speed V of the sprocket has reached the sublimit V1 (step S32). When the control unit 35 determines that the rotating speed V of the sprocket has reached the sublimit V1, the control unit 35 transmits a lighting signal so as to light the warning lamp (step S33). Thus, the control unit 35 notifies that the driving state of the motor 32 is approaching the limit and the sprocket 37 is beginning to bring about an excessive bending speed.

Furthermore, the control unit 35 determines whether the rotating speed V of the sprocket has reached the limit V2 (step S34). When the control unit 35 determines that the rotating speed V of the sprocket has reached the limit V2, the control unit 35 stops the motor 32 or inactivates the clutch so as to bring the bending section 12 to the bending operation wires-freed state (step S35) in the same manner as described in relation to the first embodiment. Consequently, when the driving state of the motor 32 reaches the limit and the sprocket 37 brings about an excessive bending speed, the control unit 35 does not permit transmission of driving force exerted by the motor 32 to the sprocket 31.

On the other hand, when the results of comparison sent from the comparison unit 43d demonstrate that the rotating speed V of the sprocket is equal to or smaller than the sublimit V1 or ranges from the sublimit V1 to the limit V2, the control unit 35 extends control so that the bending section 12 will be bent normally (step S36).

Consequently, the rotating speed of the sprocket 31 incorporated in the electric bending endoscope 2 of the present variant is detected and compared with the pre-recorded limits. When the rotating speed of the sprocket reaches the sublimit, the fact is notified. When the rotating speed of the sprocket reaches the limit, supply of energy to the motor 32 is stopped or transmission of power exerted by the motor 32 is disconnected.

Consequently, the electric bending endoscope 2 in accordance with the present variant provides the same advantage as the third embodiment does.

Alternatively, a motor driving signal sent from the motor amplifier 34 may be controlled.

Figure 12:
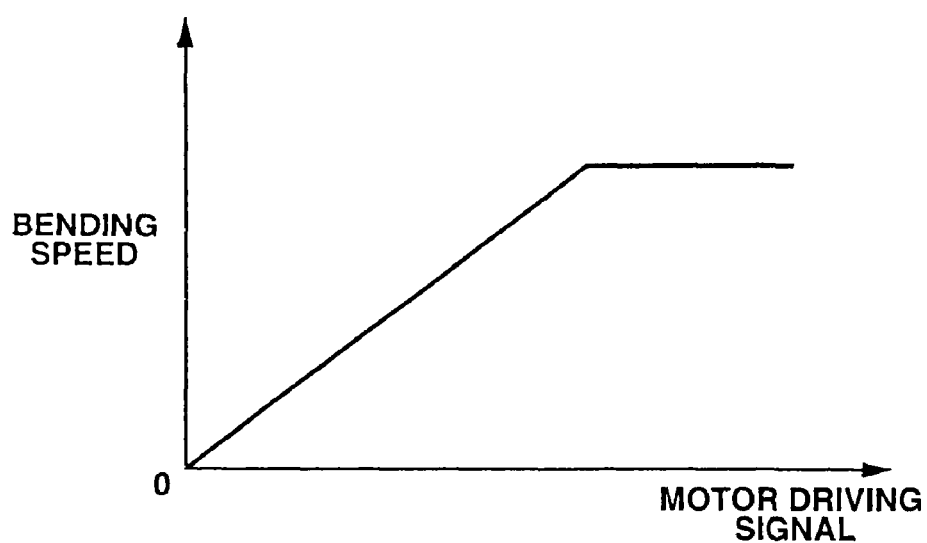
FIG. 12 is a graph indicating the bending speed of a bending section in relation to a motor driving signal that is sent from a motor amplifier under the control of a control unit.

Specifically, a predetermined rotating speed V3 of the sprocket is inputted and recorded in the record unit 42d in advance. The comparison unit 43d compares the rotating speed V of the sprocket sent from the rotating speed detection unit 71 with the recorded rotating speed of the sprocket. Based on the results of the comparison, the control unit 35 controls the motor driving signal to be sent from the motor amplifier 34. In other words, the control unit 35 controls the motor driving signal to be sent from the motor amplifier 34 so that the bending speed at which the bending section 12 is bent will remain constant as shown in FIG. 12.

In this case, when the results of comparison sent from the comparison unit 43d demonstrate that the rotating speed V of the sprocket has reached the predetermined rotating speed of the sprocket, the control unit 35 controls the motor amplifier 34 so that the rotating speed V of the sprocket will equal the predetermined rotating speed of the sprocket.

Consequently, according to the present variant, the rotating speed V of the sprocket can be suppressed to the predetermined rotating speed. The bending section 12 will therefore, not be bent without operator's intention.

Otherwise, a bending operation speed signal produced by the bending operation input unit 20 included in the electric bending endoscope may be controlled.

Figure 13:
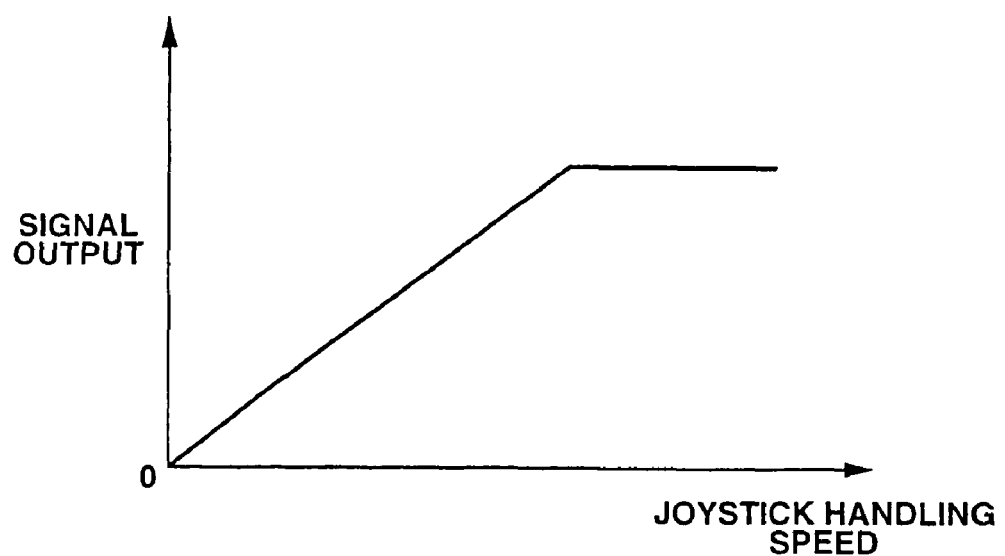
FIG. 13 is a graph indicating a handling speed signal sent from a joystick in relation to a handling speed at which the joystick is handled under the control of the control unit.

Specifically, the control unit 35 controls the bending operation input unit 20 so that the bending operation speed signal produced by the bending operation input unit 20 such as a joystick, or the like will remain constant as shown in FIG. 13. When a handling speed at which the bending operation input unit 20 is handled reaches a predetermined handling speed, the control unit 35 controls the bending operation input unit 20 so that the bending operation speed signal produced by the bending operation input unit 20 will be equal to a predetermined bending operation speed signal.

Figure 14:
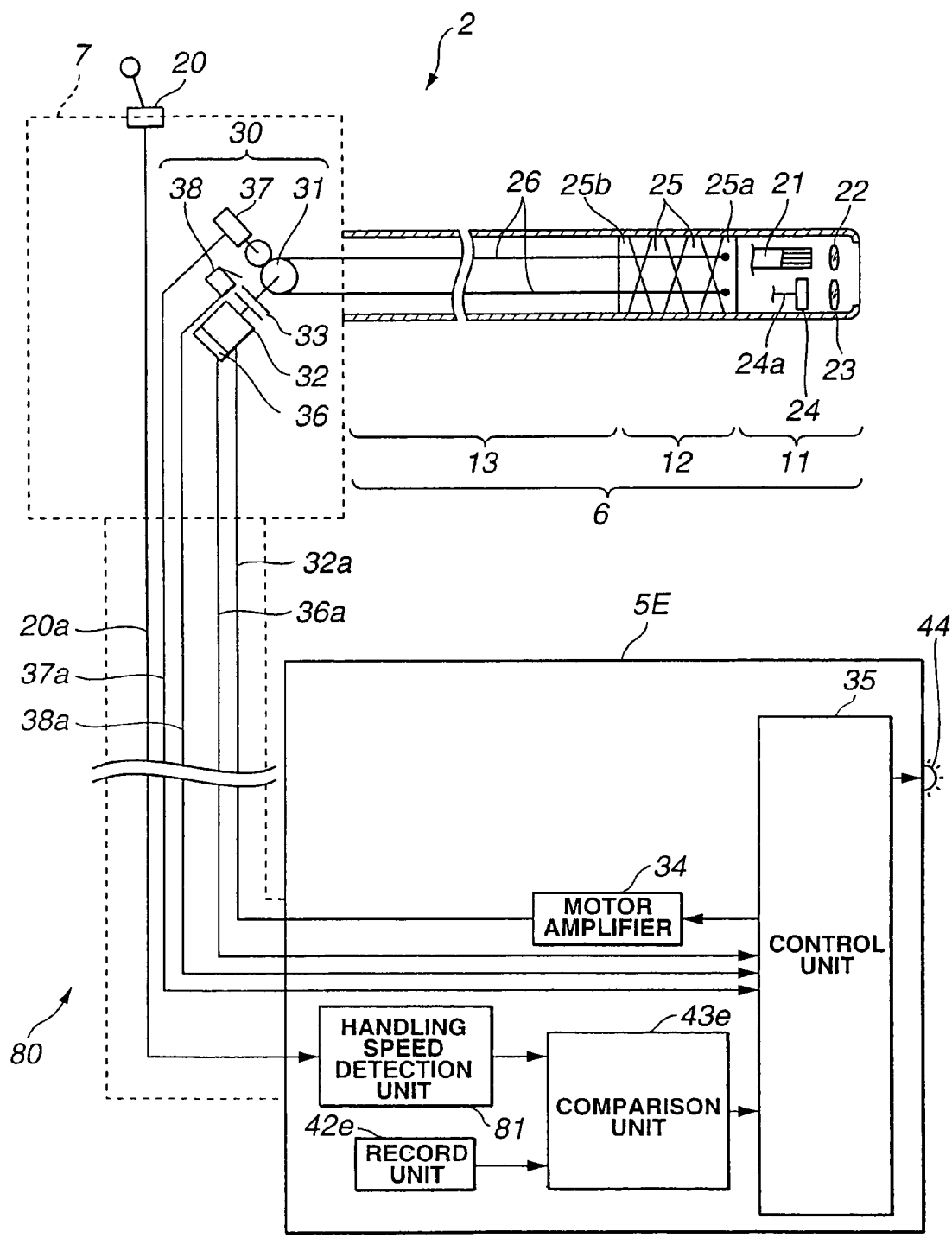
FIG. 14 shows the outline configuration of a variant of an electric bending endoscope system which extends control according to the graph of FIG. 13.

In this case, as shown in FIG. 14, an electric bending endoscope system 80 is configured so that a handling speed at which the bending operation input unit 20 is handled will be measured or detected using a potentiometer that is not shown. A handling speed detection unit 81 included in a bending control unit 5E acquires the data of the handling speed. The handling speed is then compared with a recorded predetermined handling speed.

Specifically, a predetermined handling speed at which the bending operation input unit 20 included in the electric bending endoscope 2 is handled is inputted in advance and recorded in a record unit 42e. A comparison unit 43e compares the recorded handling speed with the handling speed sent from the handling speed detection unit 81. Based on the results of the comparison, the control unit 35 controls a bending operation speed signal sent from the bending operation input unit 20.

Consequently, according to the present variant, a handling speed signal sent from the bending operation input unit 20 can be suppressed to a predetermined bending operation speed signal. The bending section 12 will not be bent without operator's intention.

Fourth Embodiment

Figure 15:
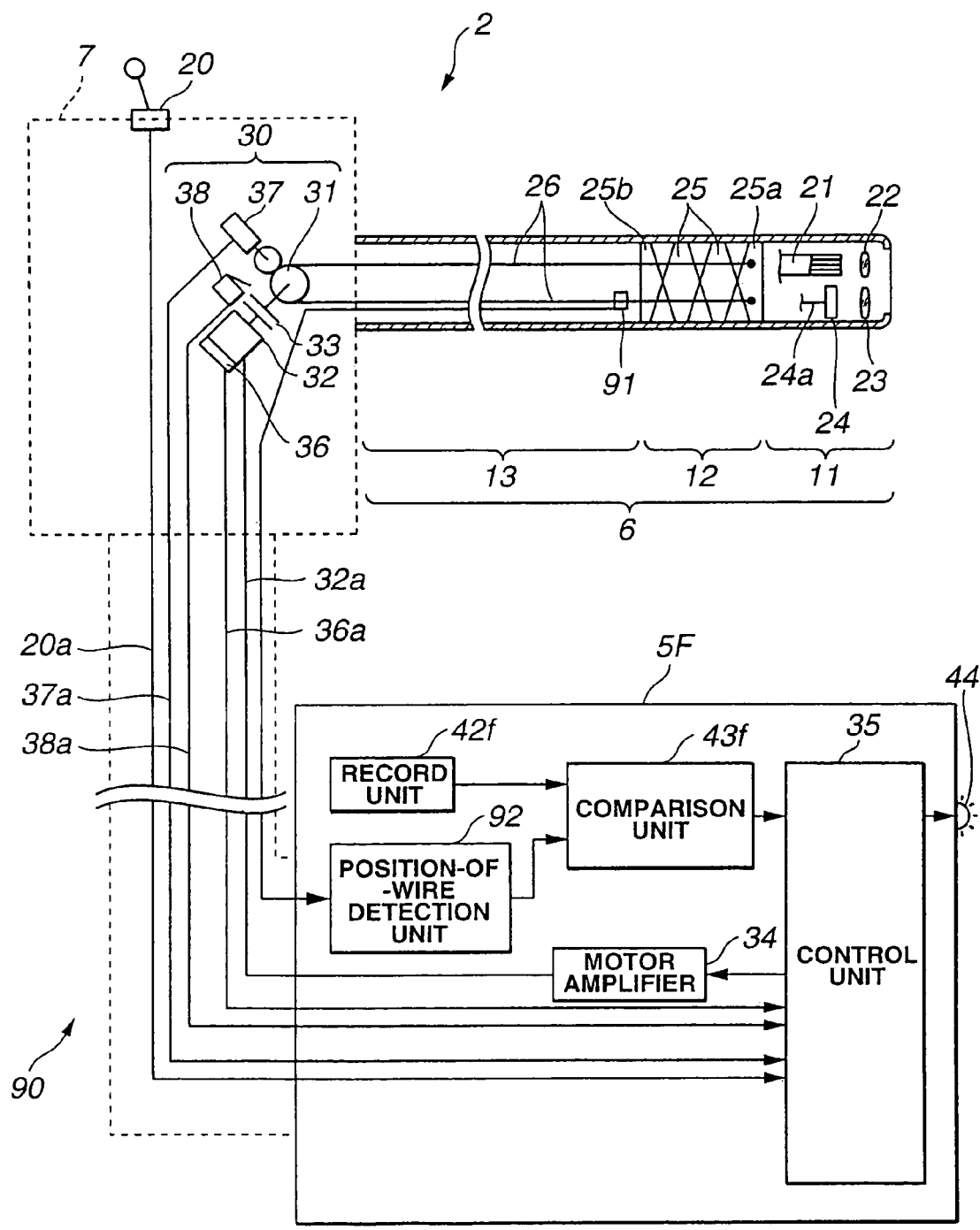
FIG. 15 shows the outline configuration of an electric bending endoscope system including a fourth embodiment of the present invention.
Figure 16:
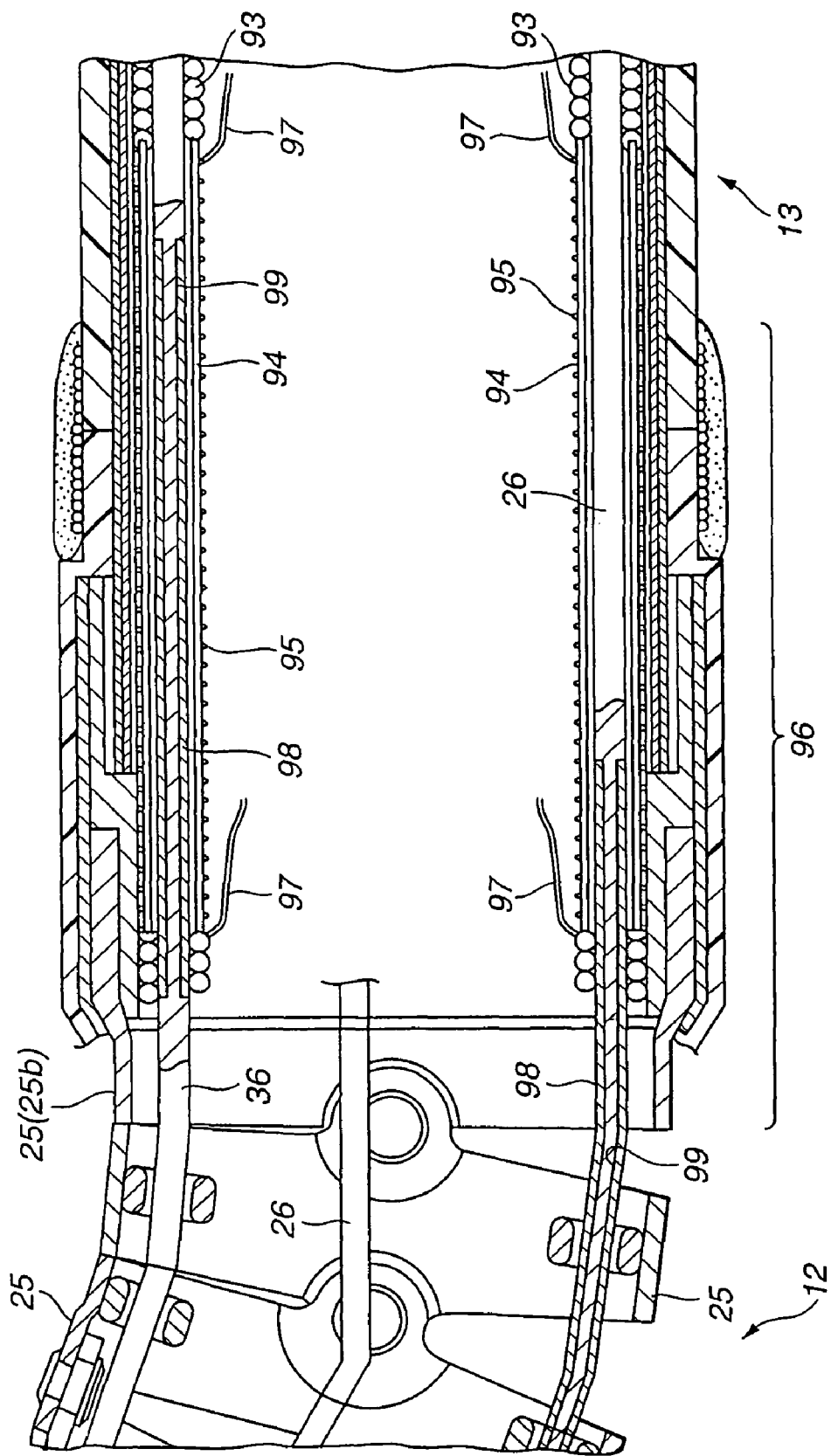
FIG. 16 is a longitudinal sectional view showing the joint of a bending section and a flexible tube, which are included in the electric bending endoscope system shown in FIG. 15, and its surroundings.
Figure 17:
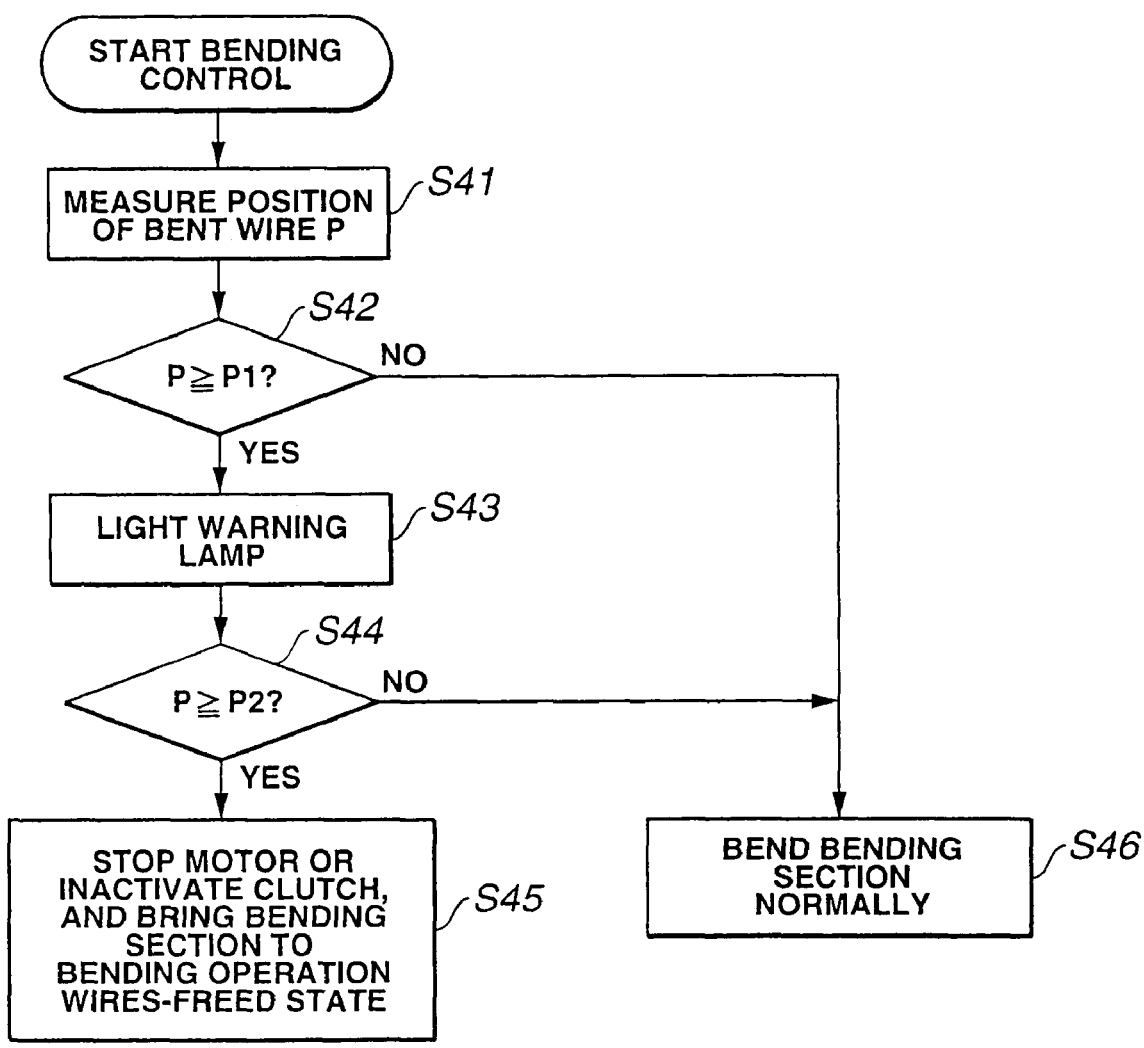
FIG. 17 is a flowchart describing bending control performed in the electric bending endoscope system shown in FIG. 15.

FIG. 15 to FIG. 17 are concerned with a fourth embodiment of the present invention.

According to the fourth embodiment, positions to which the bending operation wires 26 are bent are detected as state values indicating the driving state of the bending drive unit 30, and compared with recorded limits. The other constituent features are identical to those of the first embodiment. The description of the constituent features will be omitted. Components identical to those of the first embodiment will be described with the same reference numerals assigned thereto.

As shown in FIG. 15, an electric bending endoscope system 90 including the fourth embodiment is configured so that positions to which the bending operation wires 26 are bent will be detected as state values indicating the driving state of the bending drive unit 30 and compared with recorded limits.

To be more specific, the electric bending endoscope 2 has a displacement-of-bending operation wire sensor (hereinafter, a displacement sensor) 91, which detects the positions to which the bending operation wires 26 are bent as state values indicating the driving state of the bending drive unit 30, incorporated in the flexible tube 13 thereof. A bending control device 5F comprises: a position-of-wire detection unit 92 that receives the data of the positions to which the bending operation wires are bent that are detected by the displacement sensor 91; a record unit 42f in which the limits of the positions to which the bending operation wires are bent that are inputted in advance are recorded; and a comparison unit 43f that compares the data of the positions, to which the bending operation wires are bent that are detected by the position-of-wire detection unit 92, with the limits of the positions to which the bending operation wires are bent that are recorded in the record unit 42f.

The position-of-wires detection unit 92 receives the data of the positions to which the bending operation wires are bent, which are detected by the displacement sensor 91, as the bent positions P, and transmits the bent positions P to the comparison unit 43f. Incidentally, the bent positions P are state values equivalent to the one indicating an angle by which the bending section 12 is bent.

In the record unit 42f, a sublimit P1 immediately preceding a limit and the limit P2 that are inputted in advance are recorded as the limits of the positions to which the bending operation wires are bent. The recorded limits are transmitted to the comparison unit 43f.

The comparison unit 43f compares the bent position P sent from the position-of-wire detection unit 92 with the sublimit P1 and limit P2 read from the record unit 42f, and transmits the results of the comparison to the control unit 35.

The position-of-bending operation wire detection unit 91, record unit 42f, and comparison unit 43f are connected to the control unit 35, though the connections are not shown. The position-of-bending operation wire detection unit 91, record unit 42f, and comparison unit 43f are controlled with control signals sent from the control unit 35. Incidentally, the position-of-bending operation wire detection unit 91, record unit 42f, and comparison unit 43f may be realized with software and installed in the control unit 35.

The control unit 35 controls, as described in the flowchart of FIG. 17 that will be described later, the notification unit 44 according to the results of comparison sent from the comparison unit 43f. When the positions to which the bending operation wires 26 are bent reach the limit, the control unit 35 stops the motor 32 or brings the bending section 12 to the bending operation wires-freed state.

Next, referring to FIG. 16, the displacement sensor 91 incorporated in the flexible tube 13 will be described below.

As shown in FIG. 16, the displacement sensor 91 has sensor coils incorporated in coil sheaths 93 through which the respective bending operation wires 26 lie and which guide the bending operation wires. A coil wire used to create the coil sheaths 93 is made of a low-permeability magnetic substance such as a stainless steel or tungsten or a non-magnetic substance. The bending operation wires 26 are also made of a similar low-permeability magnetic substance or non-magnetic substance.

The coil sheath 93 has part of the coil wire, which is located near the distal end thereof, removed. A thin pipe 94 made of a low-permeability magnetic substance such as a stainless steel or a non-magnetic substance is fitted in the removed part of the coil sheath 93. The pipe 94 is arranged coaxially to the coil sheath 93. The distal and rear ends of the pipe 94 are spliced to the coil wire of the coil sheath 93. Thus, the pipe 94 is integrated with the coil sheath 93 in order to form a guide sheath. The pipe 94 does not interrupt movement of each bending operation wire 26. The pipe 94 is also made of a similar low-permeability magnetic substance or non-magnetic substance. Moreover, the pipe 94 is so thin as to be bent. The pipe 94 as well as the coil sheath 93 will not impair the flexibility of the flexible tube.

The pipe 94 is sheathed with a sensor coil 95. The sensor coil 95 is wound about the pipe 94 while being electrically isolated therefrom. An insulating material or the like may be applied to the periphery of the sensor coil 95.

The sensor coil 95 has leads 97 extended from both the ends thereof. The leads 97 are led to the angling connector 9c of the universal cord 8, and then led to the position-of-wire detection unit 92 included in the bending control device 5 over the connection cable 5a. Incidentally, the position-of-wire detection unit 92 applies an alternating voltage to the sensor coils 95. A resonant capacitor that is not shown is used to detect a change in a voltage across both the ends of each of the sensor coils. This realizes an inductance detection unit that detects a change in inductance offered by each of the sensor coils 95 in the form of a change in voltage.

Parts of the bending operation wires 26 that meet the sensor coils 95 have the peripheries thereof coated with a magnetic material 98 and are thus formed as magnetic parts 98. For formation of the magnetic parts 98, the bending operation wires 26 must not be thick. Therefore, the bending operation wires 26 have a small-diameter part 99 formed over a certain length along the axis of each wire. The peripheries of the small-diameter parts 99 are coated with the magnetic material.

The displacement sensor 91 has the foregoing components. Herein, when the bending section 12 is bent, the bending operation wires 26 are drawn or released similarly to those described in relation to the first embodiment. Consequently, the magnetic parts 98 move within the respective sensor coils 95. This causes a permeability to change. Accordingly, the inductance offered by each of the sensor coils 95 included in the displacement sensor 91 changes, and the voltage across both the ends of the sensor coil 95 varies. Eventually, the positions to which the bending operation wires 26 are bent are detected as an output to be sent to the position-of-wire detection unit 92.

The electric bending endoscope 2 is, similarly to the one described in relation to the first embodiment, connected to the light source device 3, video processor 4, and bending control device 5F, and used for endoscopic examination or the like.

An operator holds the grip 7a of the electric bending endoscope 2 so as to perform endoscopic examination. During the endoscopic examination, the operator handles the bending operation input unit 20 such as a joystick, or the like so as to bend the bending section 12.

When the bending section of the electric bending endoscope 2 is bent over a prolonged period of time, the driving state of the motor 32 approaches the limit. The bent positions P to which the bending operation wires 26 are bent imply excessive bending operation. At this time, the electric bending endoscope 2 has the bending section 12 thereof controlled as described in the flowchart of FIG. 17.

As described in FIG. 17, the position-of-wire detection unit 92 measures or detects as the bent positions P the data of the positions to which the bending operation wires are bent that is sent from the displacement sensor 91 (step S41). The position-of-wire detection unit 92 then transmits the detected bent positions P to the comparison unit 43f in response to an output signal sent from the control unit 35.

On the other hand, from the record unit 42f, the recorded sublimit P1 and limit P2 of the positions to which the bending operation wires are bent are transmitted to the comparison unit 43f in response to an output signal sent from the control unit 35.

The comparison unit 43f compares the bent positions P, which are sent from the position-of-wire detection unit 92, with the sublimit P1 and limit P2 read from the record unit 42f, and transmits the results of the comparison to the control unit 35.

The control unit 35 determines based on the results of comparison sent from the comparison unit 43f whether the bent positions P have reached the sublimit P1 (step S42). When the control unit determines that the bent positions P have reached the sublimit P1, the control unit 35 transmits a lighting signal so as to light the warning lamp (step S43). Thus, the control unit 35 notifies that the driving state of the motor 32 is approaching the limit and the bent positions P are beginning to imply excessive bending operation.

Furthermore, the control unit 35 determines whether the bent positions P have reached the limit P2 (step S44). When control unit 35 determines that the bent positions P have reached the limit P2, the control unit 35 stops the motor 32 or inactivates the clutch so as to bring the bending section 12 to the bending operation wires-freed state in the same manner as the one described in relation to the first embodiment (step S45). Consequently, when the driving state of the motor 32 reaches the limit and the bent positions P to which the bending operation wires 26 are bent imply excessive bending operation, the control unit 35 does not permit transmission of driving force exerted by the motor 32 to the sprocket 31.

On the other hand, when the results of comparison sent from the comparison unit 43f demonstrate that the bent positions P are equal to or smaller than the sublimit P1 or ranges from the sublimit P1 to the limit P2, the control unit 35 extends control so that the bending section 12 will be bent normally (step S46).

Consequently, the positions to which the bending operation wires 26 incorporated in the electric bending endoscope 2 in accordance with the fourth embodiment are bent are detected and compared with the pre-recorded limits. When the positions to which the bending operation wires are bent reach the sublimit, the fact is notified. When the positions to which the bending operation wires are bent reach the limit, supply of energy to the motor 32 is stopped or transmission of power exerted by the motor 32 is disconnected.

The electric bending endoscope 2 in accordance with the fourth embodiment provides the same advantage as the one of the first embodiment.

Fifth Embodiment

FIG. 18 to FIG. 23B are concerned with a fifth embodiment of the present invention.

According to the fourth embodiment, the positions to which the bending operation wires 26 are bent are detected as state values indicating the driving state of the bending drive unit 30, and compared with the recorded limits. According to the fifth embodiment, the tensions of the bending operation wires 26 are detected as state values indicating the driving state of the bending drive unit 30, and compared with recorded limits. The other constituent features are identical to those concerning the first embodiment. The description of the constituent features will be omitted. Components identical to those concerning the first embodiment will be described with the same reference numerals assigned thereto.

Figure 18:
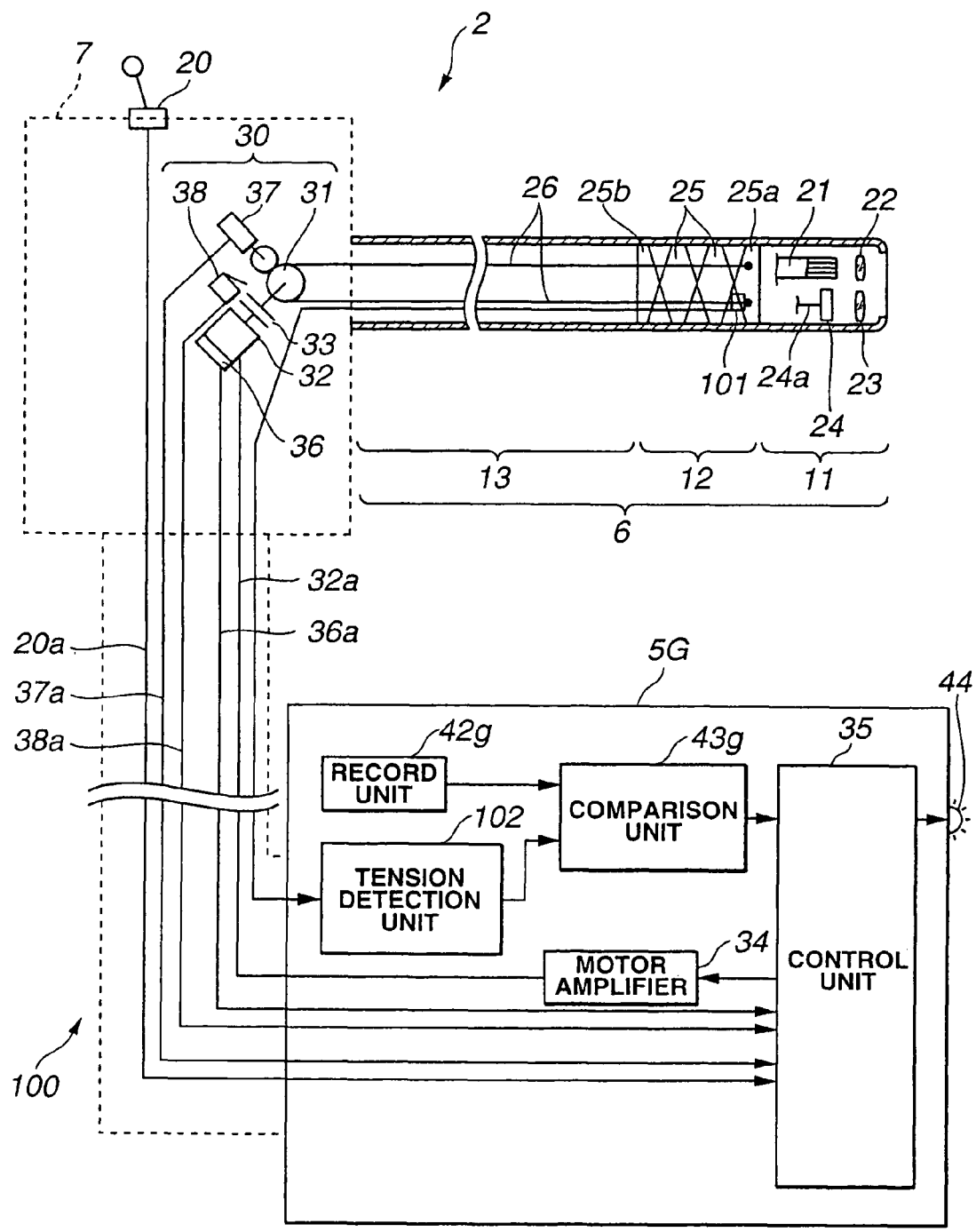
FIG. 18 shows the outline configuration of an electric bending endoscope system including a fifth embodiment of the present invention.

A shown in FIG. 18, an electric bending endoscope system 100 including the fifth embodiment is configured so that the tensions of the bending operation wires 26 will be detected as state values indicating the driving state of the bending drive unit 30, and compared with recorded limits.

To be more specific, the electric bending endoscope 2 includes a tension-of-bending operation wire sensor (hereinafter, tension sensor) 101 incorporated in the distal section 11 thereof. The tension sensor 101 detects the tensions of the bending operation wires 26 as state values indicating the driving state of the bending drive unit 30. A bending control device 5G includes: a tension detection unit 102 that acquires the data of the tensions detected by the tension sensors 101; a record unit 42g in which the limits of tension that are inputted in advance are recorded; and a comparison unit 43g that compares the data of the tensions sent from the tension detection unit 102 with the limits of tension recorded in the record unit 42g.

The tension detection unit 102 acquires the data of the tensions detected by the tension sensor 101 as tensions T, and transmits the tensions T to the comparison unit 43g.

In the record unit 42g, a sublimit T1 immediately preceding a limit and the limit T2 that are inputted in advance are recorded as the limits of tension. The recorded limits are transmitted to the comparison unit 43g.

The comparison unit 43g compares the tensions T sent from the tension detection unit 102 with the sublimit T1 and limit T2 read from the record unit 42g, and transmits the results of the comparison to the control unit 35.

The tension detection unit 91, record unit 42g, and comparison unit 43g are connected to the control unit 35, though the connections are not shown. The tension detection unit 91, record unit 42g, and comparison unit 43g are controlled based on control signals sent from the control unit 35. Incidentally, the tension detection unit 91, record unit 42g, and comparison unit 43g may be realized with software and installed in the control unit 35.

The control unit 35 controls, as described in the flowchart of FIG. 20 that will be referred to later, the notification unit 44 according to the results of comparison sent from the comparison unit 43g. When the tensions of the bending operation wires 26 reach the limit, the control unit stops the motor 32 or brings the bending section 12 to the bending operation wires-freed state.

Next, referring to FIG. 19A and FIG. 19B, the tension sensor 101 incorporated in the distal section 11 will be described below.

Figure 19A:
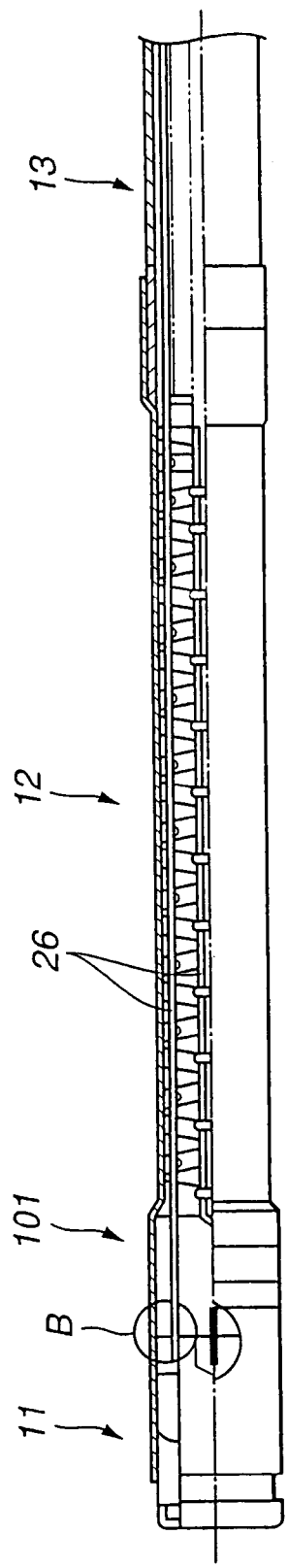
FIG. 19A is a partly sectional view showing an endoscope insertion unit.
Figure 19B:
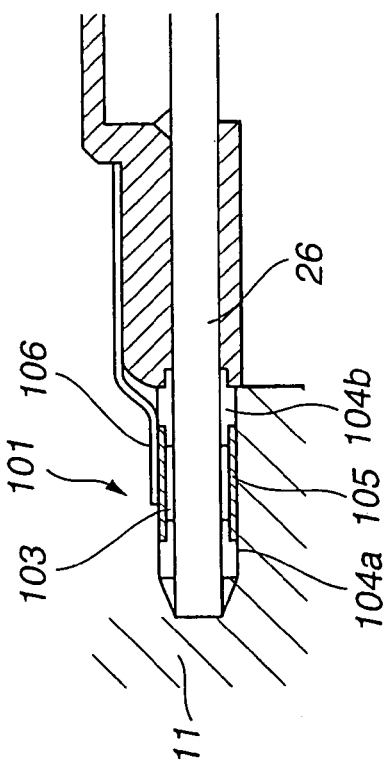
FIG. 19B is a schematic sectional view showing a tension sensor included in the insertion unit shown in FIG. 19A.

As shown in FIG. 19A and FIG. 19B, the tension sensor 101 is incorporated in the distal section 11 coupled to the distal end of the bending section 12. The tension sensor 101 has mounting holes 103 formed in an axial direction along the periphery of the distal section 11 so that the four bending operation wires 26 will be passed through the respective mounting holes 103. A pair of locking rings 104a and 104b fitted in each of the mounting holes 103 while being separated from each other in the axial direction. A strain generator 105 realized with a thin cylinder is sandwiched between the locking rings 104a and 104b.

The locking rings 104a and 104b and the strain generator 105 have one of the bending operation wires 26 penetrated through them. Each of the bending operation wires 26 has the distal end thereof locked in the locking ring 104a. Furthermore, the strain generator 105 has a strain gauge 106 fixed to the periphery thereof.

The tension sensor 101 has the foregoing components. When the bending section 12 is bent, the bending operation wires 26 are drawn or released in the same manner as described in relation to the first embodiment. Consequently, the strain generators 105 are tensed and compressed in the axial direction. A strain is generated. The strain gauges 106 included in the tension sensor 101 detect degrees of strains, that is, the tensions of the bending operation wires 26.

The data of the tensions detected by the tension sensor 101 is, similarly to the counterpart detected in the fourth embodiment, transmitted to the tension detection unit 102 included in the bending control unit 5G over a signal line that is not shown. The data of the tensions is received as tensions T.

The electric bending endoscope 2 having the foregoing structure is, similarly to the one described in relation to the first embodiment, connected to the light source device 3, video processor 4, and bending control device 5F, and used for endoscopic examination or the like.

An operator holds the grip 7a of the electric bending endoscope 2 so as to perform endoscopic examination. During the endoscopic examination, the operator handles the bending operation input unit 20 such as a joystick, or the like so as to bend the bending section 12.

When the bending section of the electric bending endoscope 2 is bent over a prolonged period of time, the driving state of the motor 32 approaches the limit. The tensions T of the bending operation wires 26 bring about excessive bending force. At this time, the electric bending endoscope 2 has the bending of the bending section 12 thereof controlled as described in the flowchart of FIG. 20.

Figure 20:
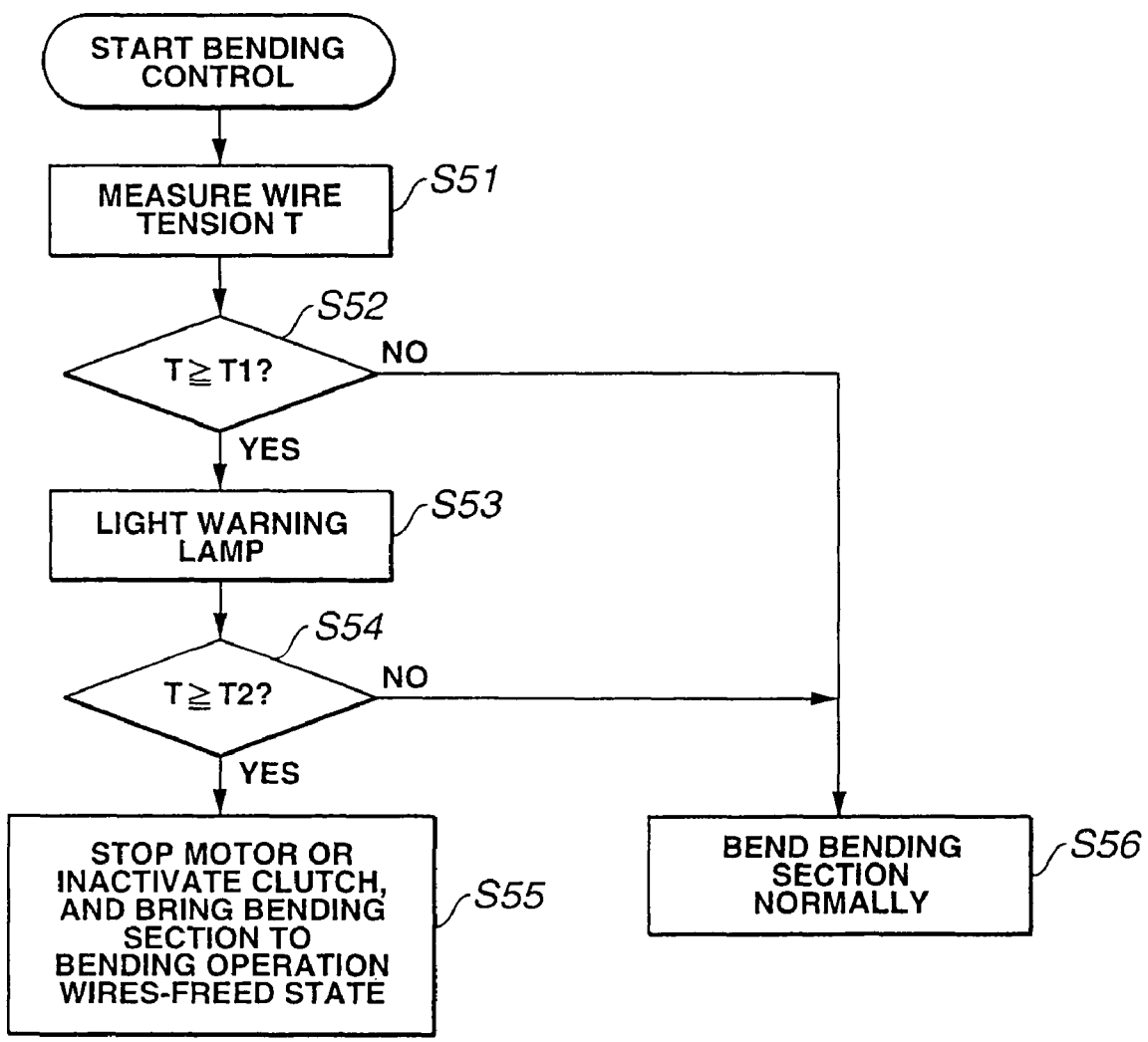
FIG. 20 is a flowchart describing bending control to be performed in the electric bending endoscope system shown in FIG. 18.

As described in FIG. 20, the tension detection unit 102 measures or detects the data of tensions sent from the tension sensor 101 as tensions T (step S51), and transmits the detected tensions T to the comparison unit 43g in response to an output signal sent from the control unit 35.

On the other hand, from the record unit 42g, the recorded sublimit T1 and limit T2 of tension are transmitted in response to an output signal sent from the control unit 35.

The comparison unit 43g compares the tensions T sent from the tension detection unit 102 with the sublimit T1 and limit T2 read from the record unit 42g, and transmits the results of the comparison to the control unit 35.

The control unit 35 determines based on the results of comparison sent from the comparison unit 43g whether the tensions T have reached the sublimit T1 (step S52). When the control unit 35 determines that the tensions T have reached the sublimit T1, the control unit 35 transmits a lighting signal so as to light the warning lamp (step S53). Thus, the control unit 35 notifies that the driving state of the motor 32 is approaching the limit and the tensions T of the bending operation wires 26 are beginning to bring about excessive bending force.

Furthermore, the control unit 35 determines whether the tensions T have reached the limit T2 (step S54). When the control unit 35 determines that the tensions T have reached the limit T2, the control unit 35 stops the motor 32 or inactivates the clutch so as to bring the bending section 12 to the bending operation wires-freed state in the same manner as the one described in relation to the first embodiment (step S55). Consequently, when the driving state of the motor 32 reaches the limit and the tensions T of the bending operation wires 26 bring about excessive bending force, the control unit 35 does not permit transmission of driving force exerted by the motor 32 to the sprocket 31.

On the other hand, when the results of comparison sent from the comparison unit 43g demonstrate that the tensions T are equal to or lower than the sublimit T1 or range from the sublimit T1 to the limit T2, the control unit 35 extends control so that the bending section 12 will be bent normally (step S56).

Consequently, the tensions of the bending operation wires 26 included in the electric bending endoscope 2 in accordance with the fifth embodiment are detected and compared with the pre-recorded limits. When the tensions reach the sublimit, the fact is notified. When the tensions reach the limit, supply of energy to the motor 32 is stopped or transmission of power exerted by the motor 32 is disconnected.

Consequently, the electric bending endoscope 2 in accordance with the fifth embodiment provides the same advantage as the first embodiment does.

Figure 21A:
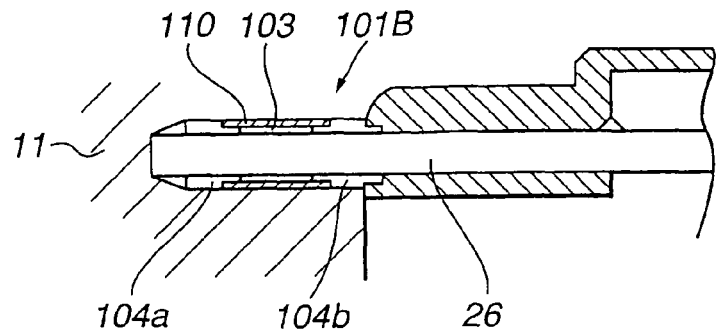
FIG. 21A is a sectional view schematically showing a tension sensor of a first variant.
Figure 21B:
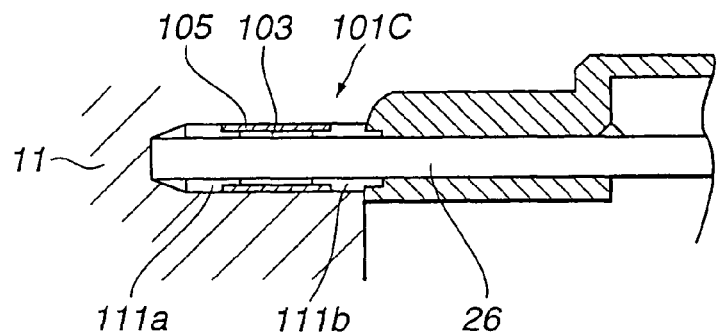
FIG. 21B is a sectional view schematically showing a tension sensor of a second variant.

The tension sensor may be structured as shown in FIG. 21A or FIG. 21B.

As shown in FIG. 21A, a tension sensor 101B has strain generators 105 thereof realized with piezoelectric devices 110 but does not include the strain gauges 106.

When the bending section 12 is bent, the bending operation wires 26 are drawn or released in the same manner as described in relation to the first embodiment. The strain generators 105 included in the tension sensor 101B are tensed, and then compressed in an axial direction. This causes a strain. A voltage is then developed in the piezoelectric devices 110 included in the tension sensor 101B. The developed voltages are transmitted to the tension detection unit 102, whereby the tensions of the bending operation wires 26 can be detected.

As shown in FIG. 21B, a tension sensor 101C has a pair of electrode plates 111a and 111b at both ends of each strain generator 105.

When the bending section 12 is bent, the bending operation wires 26 are drawn or released in the same manner as described in relation to the first embodiment. The strain generators 105 included in the tension sensor 101C are then tensed, and compressed in an axial direction. This causes a strain. The distance between each pair of electrode plates 111a and 111b changes, whereby an electrostatic capacitance-dependent voltage varies. The variations of the voltages are transmitted to the tension detection unit 102. Consequently, the tensions of the bending operation wires 26 can be detected.

Figure 22A:
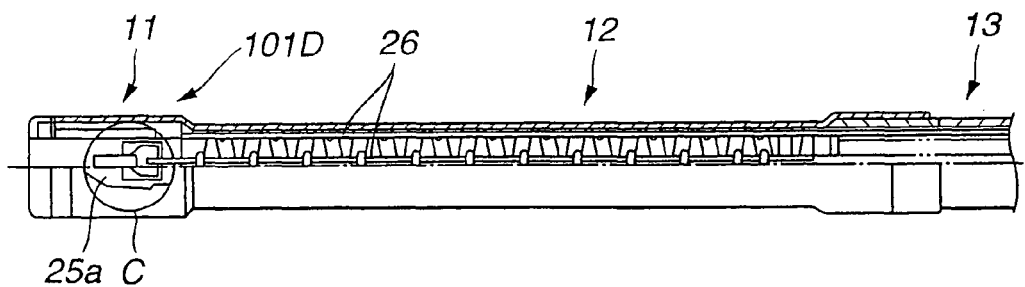
FIG. 22A is a partly sectional view showing an endoscope insertion unit that is a variant of the endoscope insertion unit shown in FIG. 19A.
Figure 22B:
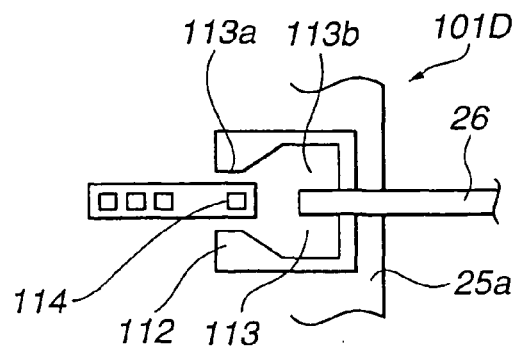
FIG. 22B is a sectional view schematically showing a tension sensor shown in FIG. 22A.

Moreover, the tension sensor may be structured as shown in FIG. 22A and FIG. 22B.

As shown in FIG. 22A and FIG. 22B, a tension sensor 101D has a notch 112, which is shaped substantially like a bracket, formed in parts of the leading bending piece 25a that meet the respective bending operation wires 26. A tongue-like wire coupler 113 is enclosed in each of the notches 112 included in the tension sensor 101D, and has a neck 113a and a head 113b. The distal part of each of the bending operation wires 26 is coupled to the head 113 of each of the wire couplers 113 included in the tension-sensor 101D. Moreover, a strain gauge 114 is attached to each of the necks 113a.

When the bending section 12 is bent, the bending operation wires 26 are drawn or released in the same manner as described in relation to the first embodiment. The wire couplers 113 included in the tension sensor 101D are then tensed. Consequently, the necks 113a are strained. The strain gauges 114 included in the tension sensor 101D detect degrees of strains, that is, the tensions of the bending operation wires 26.

Figure 23A:
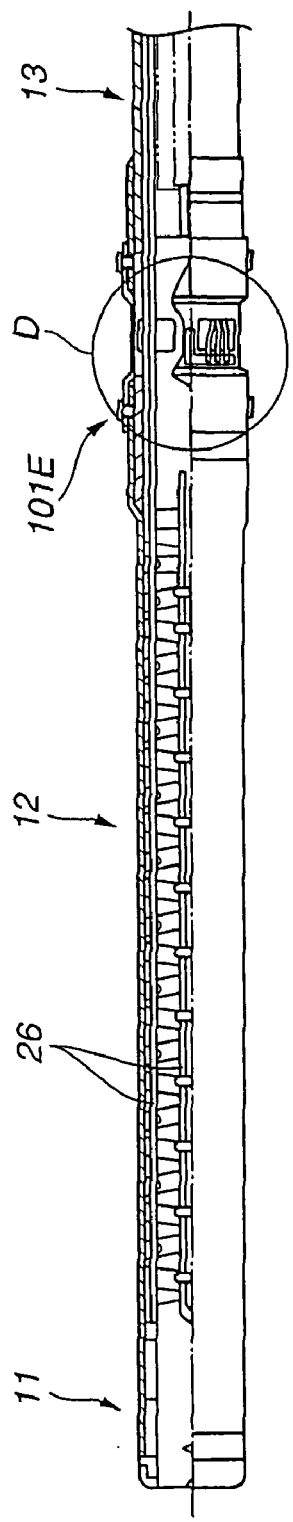
FIG. 23A is a partly sectional view showing an endoscope insertion unit that is another variant of the endoscope insertion unit shown in FIG. 19A.
Figure 23B:
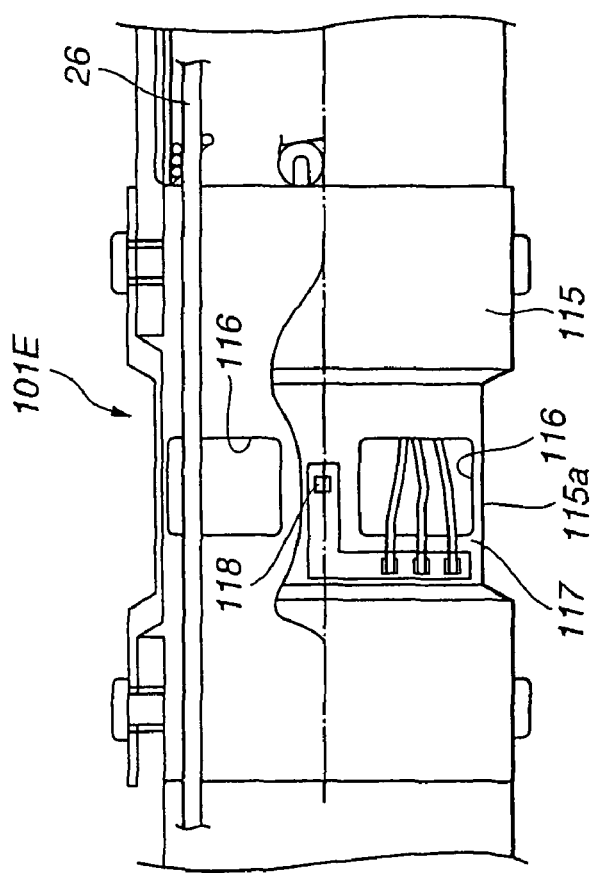
FIG. 23B is a sectional view schematically showing the tension sensor shown in FIG. 23A.

The tension sensor may be structured as shown in FIG. 23A and FIG. 23B.

As shown in FIG. 23A and FIG. 23B, a joint tube 115 that is a joint of the flexible tube 13 and bending section 12 has a small-diameter portion 115a extended in the middle thereof in an axial direction. An opening window 116 is formed at positions on the outer wall of the small-diameter portion 115a corresponding to the positions of the respective bending operation wires 26. The formation of the opening windows 116 provides the small-diameter portion 115a with strain generators 117.

Moreover, a strain gauge 118 is disposed near each of the opening windows 116 of the strain generators 117 included in the tension sensor 101E.

The tension sensor 101E has the foregoing structure. When the bending section 12 is bent, the bending operation wires 26 are drawn or released in the same manner as the ones described in relation to the first embodiment. The strain generators 117 located near the respective bending operation wires 26 are compressed. Consequently, the strain generators 117 deflect and strain. The strain gauges 118 detect the degrees of strains, that is, the tensions of the bending operation wires 26.

Sixth Embodiment

Figure 24:
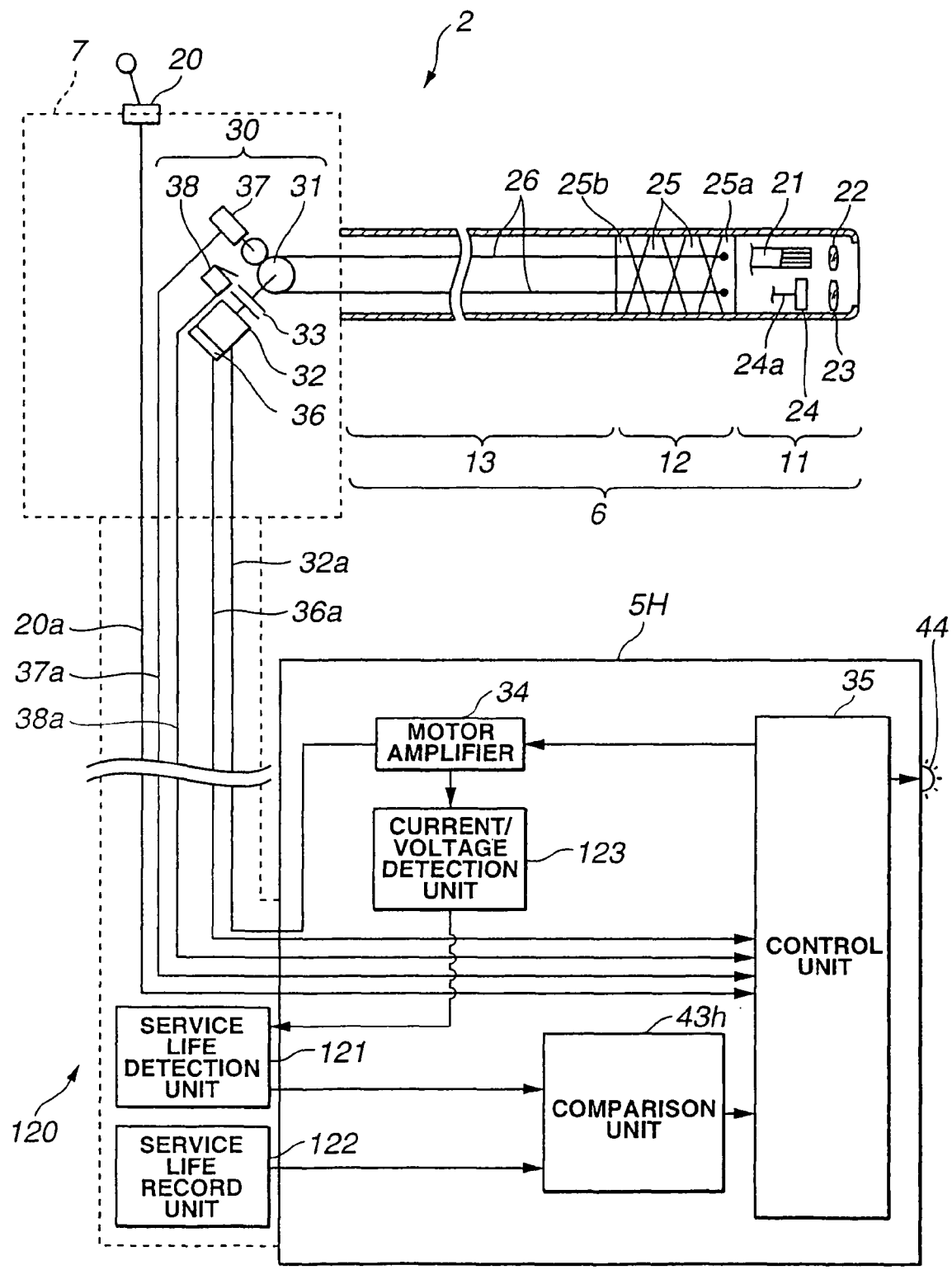
FIG. 24 schematically shows the configuration of an electric bending endoscope system including a sixth embodiment of the present invention.

FIG. 24 and FIG. 25 are concerned with a sixth embodiment of the present invention.

According to the sixth embodiment, the mechanical service life of the motor 32 is detected as a state value indicating the driving state of the bending drive unit 30, and compared with recorded limits. The other constituent features are identical to those of the first embodiment. The description of the constituent features will therefore be omitted. Components identical to those of the first embodiment will be described with the same reference numerals assigned thereto.

As shown in FIG. 24, an electric bending endoscope system 120 including the sixth embodiment is configured so that the mechanical use time of the motor 32 will be detected as a state value indicating the driving state of the bending drive unit 30 and compared with recorded limits.

To be more specific, the electric bending endoscope 2 has a service life detection unit 121 and a service life record unit 122 incorporated in the angling connector 9c thereof. The service life detection unit 121 detects the mechanical use time of the motor 32 as a state value indicating the driving state of the bending drive unit 30. The mechanical use time of the motor 32 detected by the service life detection unit 121 and the limits of mechanical use time inputted in advance are recorded in the service life record unit 122. A bending control device 5H includes a comparison unit 43h that compares the data of the mechanical use time detected by the service life detection unit 121 with the limits of mechanical use time recorded in the service life record unit 122.

Furthermore, the bending control device 5H includes a current/voltage detection unit 123 that detects a current and a voltage which serve as a motor driving signal to be sent from the motor amplifier 34. The data of the detected current and voltage are received as a current i and a voltage v respectively, and transmitted to the service life detection unit 121.

The service life detection unit 121 calculates a mechanical use time LT from the current i and voltage v sent from the current/voltage detection unit 123 and a use time Δt. The previous mechanical use time LT is updated with the calculated value, and the calculated value is transmitted to the comparison unit 43h. Incidentally, the mechanical use time may be calculated from the tension T, which is provided by the tension sensor 101 and tension detection unit 102 as described in relation to the fifth embodiment, and the use time Δt.

In the service life record unit 122, a sublimit LT1 immediately preceding a limit and the limit L2 that are inputted in advance are recorded as the limits of mechanical use time. The recorded limits are transmitted to the comparison unit 43h.

The comparison unit 43h compares the mechanical use time LT sent from the service life detection unit 121 with the sublimit LT1 and limit LT2 read from the service life record unit 122, and transmits the results of the comparison to the control unit 35.

The service life detection unit 121, service life record unit 122, comparison unit 43h, and current/voltage detection unit 123 are connected to the control unit 35, though the connections are not shown. The service life detection unit 121, service life record unit 122, comparison unit 43h, and current/voltage detection unit 123 are controlled based on control signals sent from the control unit 35. Incidentally, the service life detection unit 121, service life record unit 122, comparison unit 43h, and current/voltage detection unit 123 may be realized with software and installed in the control unit 35.

Moreover, the service life record unit 122 may be incorporated in the bending control device 5H. The mechanical use time LT that differs from endoscope to endoscope, and the sublimit LT1 and limit LT2 may be recorded in the service life record unit 122.

The control unit 35 controls, as described in the flowchart of FIG. 25 that will be referred to later, the notification unit 44 according to the results of comparison sent from the comparison unit 43h. When the mechanical use time of the motor 32 reaches the limit, the control unit 35 stops the motor 32 or brings the bending section 12 to the bending operation wires-freed state.

The electric bending endoscope 2 having the above components is, similarly to the one in accordance with the first embodiment, connected to the light source device 3, video processor 4, and bending control device 5H, and used for endoscopic examination or the like.

An operator holds the grip 7a of the electric bending endoscope 2 so as to perform an endoscopic examination. During the endoscopic examination, the operator handles the bending operation input unit 20 such as a joystick, or the like so as to bend the bending section 12.

When the bending section 12 of the electric bending endoscope 2 is bent over a prolonged period of time, the defined use time of the motor 32 approaches the limit. At this time, the electric bending endoscope 2 has the bending of the bending section 12 thereof controlled as described in the flowchart of FIG. 25.

As shown in FIG. 25, the current/voltage detection unit 123 measures or detects the current and voltage that serve as the motor driving signal sent from the motor amplifier 34 (step S61). The current/voltage detection unit 123 receives the data of the detected current and voltage as a current i and a voltage v, and transmits the current i and voltage v to the service life detection unit 121 in response to an output signal sent from the control unit 35.

The service life detection unit 121 calculates the mechanical use time LT from the current i and voltage v sent from the current/voltage detection unit 123 and the use time Δt, and updates the previous mechanical use time LT (step S62). The service life detection unit 121 then transmits the new mechanical use time LT to the comparison unit 43h in response to an output signal sent from the control unit 35.

On the other hand, from the service life record unit 122, the recorded sublimit LT1 and limit LT2 of mechanical use time are transmitted to the comparison unit 43h in response to an output signal sent from the control unit 35.

The comparison unit 43h then compares the mechanical use time LT sent from the service life detection unit 121 with the sublimit LT1 and limit LT2 read from the service life record unit 122, and transmits the results of comparison to the control unit 35.

The control unit 35 determines based on the results of comparison sent from the comparison unit 43h whether the mechanical use time LT has reached the sublimit LT1 (step S63). When the control unit 35 determines that the mechanical use time LT has reached the sublimit LT1, the control unit transmits a lighting signal so as to light the warning lamp (step S64). Consequently, the control unit 35 notifies that the mechanical use time of the motor 32 is approaching the limit.

The control unit 35 determines whether the mechanical use time LT has reached the limit LT2 (step S65). When the control unit 35 determines that the mechanical use time LT has reached the limit LT2, the control unit 35 stops the motor 32 or inactivates the clutch so as to bring the bending section 12 to the bending operation wires-freed state in the same manner as described in relation to the first embodiment (step S66). Consequently, when the mechanical use time of the motor 32 reaches the limit, the control unit 35 does not permit transmission of driving force exerted by the motor 32 to the sprocket 31.

On the other hand, when the results of comparison sent from the comparison unit 43h demonstrate that the mechanical use time LT is equal to or smaller than the sublimit LT1 or ranges from the sublimit LT1 to the limit LT2, the control unit 35 extends control so that the bending section 12 will be bent normally (step S67).

The mechanical service life of the motor 32 incorporated in the electric bending endoscope 2 in accordance with the sixth embodiment is detected and compared with the pre-recorded limits. When the mechanical service life reaches the sublimit, the fact is notified. When the mechanical service life reaches the limit, supply of energy to the motor 32 is stopped or transmission of power exerted by the motor 32 is disconnected.

Consequently, the electric bending endoscope 2 in accordance with the sixth embodiment provides the same advantage as the first embodiment does.

According to the present invention, it is apparent that a wide range of different embodiments can be formed based on the invention without a departure from the spirit and scope of the invention. The present invention will be limited to the appended claims but not restricted to any specific embodiments.

What is claimed is:

1. An electric bending endoscope, comprising:
   an elongated insertion unit;
   a bending section formed adjacent to a distal section of the insertion unit;
   a bending drive unit for driving the bending section to bend;
   a bending operation unit for outputting a bending instruction signal for driving the bending drive unit in response to an operation by an operator;
   an operation state detection unit for detecting an operation speed of the bending operation unit;
   a record unit in which a first threshold value and a second threshold value to be compared with the operation speed are recorded, the second threshold value being larger than the first threshold value;
   a comparison unit for comparing the operation speed with the first threshold value and the second threshold value; and
   a control unit for notifying the operator of a driving state when the operation speed has reached the first threshold value, and restricting a bending operation of the bending section based on the bending instruction signal outputted by the bending operation unit when the operation speed has further reached the second threshold value.

2. The electric bending endoscope according to claim 1, wherein the bending operation unit has a moving member for outputting the bending instruction signal by a movement accompanying an operation by the operator, and the operation state detection unit detects the operation speed of the bending operation unit by detecting a moving state of the moving member.

3. The electric bending endoscope according to claim 2, wherein the moving member is a joystick for outputting the bending instruction signal depending on an inclination of the joystick; and
   the operation state detection unit detects the operation speed of the bending operation unit by detecting an inclining speed of the joystick based on the inclination angle and an inclination time period of the joystick.

4. The electric bending endoscope comprising:
   an elongated insertion unit;
   a bending section formed adjacent to a distal section of the insertion unit;
   a bending drive unit for driving the bending section to bend;
   a bending operation unit for outputting a bending instruction signal for driving the bending drive unit in response to an operation by an operator;
   an operation state detection unit for detecting an operation speed of the bending operation unit;
   a record unit in which a threshold value to be compared with the operation speed is recorded;
   a comparison unit for comparing the operation speed with the threshold value; and a control unit for restricting, on the basis of a result of comparison by the comparison unit, a bending operation of the bending section based on the bending instruction signal outputted by the bending operation unit, the control unit invalidating the bending instruction signal outputted by the bending operation unit and stopping the bending drive unit from driving the bending section when the comparison unit determines that the operation speed is higher than the threshold value.

5. The electric bending endoscope comprising:
an elongated insertion unit;
a bending section formed adjacent to a distal section of the insertion unit;
a bending drive unit for driving the bending section to bend;
a bending operation unit for outputting a bending instruction signal for driving the bending drive unit in response to an operation by an operator;
an operation state detection unit for detecting an operation speed of the bending operation unit;
a record unit in which a threshold value to be compared with the operation speed is recorded;
a comparison unit for comparing the operation speed with the threshold value; and
a control unit for restricting, on the basis of a result of comparison by the comparison unit, a bending operation of the bending section based on the bending instruction signal outputted by the bending operation unit, the control unit disconnecting transmission of driving force from the bending drive unit to the bending section when the comparison unit determines that the operation speed is higher than the threshold value.

6. The electric bending endoscope according to claim 1, wherein, when the comparison unit determines that the operation speed is higher than the second threshold value, the control unit controls the bending instruction signal outputted from the bending operation unit so that speed of bending motion of the bending section is a predetermined speed.

* * * * *